US010858616B2

(12) United States Patent
Lant et al.

(10) Patent No.: US 10,858,616 B2
(45) Date of Patent: Dec. 8, 2020

(54) DETERGENT COMPOSITION

(71) Applicant: The Procter & Gamble Company, Cincinnati, OH (US)

(72) Inventors: Neil Joseph Lant, Newcastle upon Tyne (GB); Jean-Luc Philippe Bettiol, Etterbeek (BE); Denis Alfred Gonzales, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/590,170

(22) Filed: May 9, 2017

(65) Prior Publication Data
US 2017/0321161 A1 Nov. 9, 2017

(30) Foreign Application Priority Data

May 9, 2016 (EP) .................................... 16168823

(51) Int. Cl.
| | |
|---|---|
| *C11D 3/386* | (2006.01) |
| *C12N 9/88* | (2006.01) |
| *C11D 1/94* | (2006.01) |
| *C11D 3/33* | (2006.01) |
| *C12N 9/00* | (2006.01) |
| *C11D 1/75* | (2006.01) |
| *C11D 1/90* | (2006.01) |
| *C11D 3/00* | (2006.01) |
| *C11D 3/36* | (2006.01) |

(52) U.S. Cl.
CPC ............ *C11D 3/38636* (2013.01); *C11D 1/94* (2013.01); *C11D 3/0094* (2013.01); *C11D 3/33* (2013.01); *C11D 3/364* (2013.01); *C11D 3/38672* (2013.01); *C12N 9/88* (2013.01); *C12Y 402/01053* (2013.01); *C11D 1/75* (2013.01); *C11D 1/90* (2013.01); *C12N 9/00* (2013.01)

(58) Field of Classification Search
CPC ... C11D 3/38636; C11D 3/38672; C11D 3/33; C11D 1/94; C11D 1/90; C11D 1/75; C12Y 402/01053
See application file for complete search history.

(56) References Cited

U.S. PATENT DOCUMENTS

| | | | |
|---|---|---|---|
| 5,705,465 A | 1/1998 | Angevaare | |
| 5,789,362 A | 8/1998 | Baeck | |
| 5,851,973 A * | 12/1998 | Foley | C11D 1/525 510/235 |
| 6,369,011 B1 | 4/2002 | Rai | |
| 6,372,708 B1 | 4/2002 | Kasturi | |
| 6,492,316 B1 | 12/2002 | Herbots | |
| 6,699,828 B1 | 3/2004 | De | |
| 7,456,001 B2 | 11/2008 | Christensen | |
| 8,137,477 B2 * | 3/2012 | Wittorff | C11D 3/38609 134/40 |
| 8,293,697 B2 | 10/2012 | Boutique | |
| 8,940,677 B2 * | 1/2015 | Boutique | C11D 1/83 510/276 |
| 9,834,798 B2 | 12/2017 | Piatesi | |
| 2003/0162681 A1 | 8/2003 | Hage | |
| 2003/0191043 A1 | 10/2003 | Becker | |
| 2009/0142821 A1 | 6/2009 | Cirino | |
| 2009/0203568 A1 | 8/2009 | Souter | |
| 2012/0157717 A1 | 6/2012 | Rude | |
| 2012/0227120 A1 | 9/2012 | Hitchman | |
| 2013/0175196 A1 * | 7/2013 | Dale | C11D 3/38609 206/534 |
| 2014/0322770 A1 | 10/2014 | Landvik | |
| 2015/0184208 A1 * | 7/2015 | Oestergaard | C12N 9/0065 435/67 |
| 2017/0321160 A1 | 11/2017 | Lant | |
| 2017/0321162 A1 | 11/2017 | Lant | |

FOREIGN PATENT DOCUMENTS

| | | |
|---|---|---|
| EP | 0399681 A3 | 1/1991 |
| GB | 2247025 A | 2/1992 |
| GB | 2288408 A | 10/1995 |
| JP | H09511004 A | 11/1997 |
| JP | 2001509540 A | 7/2001 |
| JP | 2003503582 A | 1/2003 |
| JP | 2004508039 A | 3/2004 |
| JP | 2005501929 A | 1/2005 |
| JP | 2015529075 A | 10/2015 |
| WO | WO9855634 A1 | 12/1998 |
| WO | WO9903962 A1 | 1/1999 |

OTHER PUBLICATIONS

Beltran et al. Influence of Harvest Date and Crop Yield on the Fatty Acid Composition of Virgin Olive Oils from Cv. Picual. J. Agric. Food Chem. 2004, 52, 3434-3440. (Year: 2004).*
Bevers et al. Oleate Hydratase Catalyzes the Hydration of a Non-activated Carbon-Carbon Bond. Journal of Bacteriology, Aug. 2009, p. 5010-5012, vol. 191, No. 15. (Year: 2009).*
Belcher, James, et al.—Structure and Biochemical Properties of the Alkene Producing Cytochrome P450 OleT JE (CYP152L1) from the *Jeotgalicoccus* sp. 8456 Bacterium*—The Journal of Biological Chemistry, vol. 289, No. 10, pp. 6535-6550, Mar. 7, 2014.

(Continued)

*Primary Examiner* — Sean C. Barron
(74) *Attorney, Agent, or Firm* — Melissa Krasovec

(57) ABSTRACT

Use of a detergent composition comprising a fatty acid-transforming enzyme to impart suds longevity in a washing process. A method for promoting suds longevity in a washing process for washing soiled articles, comprising the step of: delivering a composition comprising a fatty acid-transforming enzyme to a volume of water to form a wash liquor and immersing the soiled article in the liquor.

19 Claims, No Drawings
Specification includes a Sequence Listing.

(56) References Cited

OTHER PUBLICATIONS

Bevers, Loes E., et al.—Oleate Hydratase Catalyzes the Hydration of a Nonactivated Carbon-Carbon Bond—Journal of Bacteriology, Aug. 1, 2009, pp. 5010-5012, vol. 191, No. 15.

Davis, S. Christopher, et al.—Oxidation of w-Oxo Fatty Acids by Cytochrome P450 BM-3 (CYP102)—Archives of Biochemistry and Biophysics, vol. 328, No. 1, Apr. 1, 1996, pp. 35-42.

Engleder, Matthias, et al.—Structure-Based Mechanism of Oleate Hydratase from Elizabethkingia Meningoseptica—Chembiochem—A European Journal of Chemical Biology, Aug. 17, 2015, pp. 1730-1734, vol. 16, No. 12.

Extended European Search Report for Application No./Patent No. 16168823.9-1405, dated Nov. 24, 2016, 7 pages.

Girvan, Hazel M., et al.—Applications of Microbial Cytochrome P450 Enzymes in Biotechnology and Synthetic Biology—Current Opinion in Chemical Biology 2016, 31:136-145, www.sciencedirect.com.

International Search Report for International Application Serial No. PCT/US2017/031674, dated Jun. 28, 2017, 14 pages.

Rude, Matthew A., et al.—Terminal Olefin Biosynthesis by a Novel P450 Fatty Acid Decarboxylase from *Jeotgalicoccus* Species—Applied and Environmental Microbiology, Mar. 2011, pp. 1718-1727, vol. 77, No. 5.

Yesiloglu, Yesim, et al.—Lipase-Catalyzed Esterification of Glycerol and Oleic Acid—Journal of the American Oil Chemists Society, Mar. 1, 2004, pp. 281-284, vol. 81, No. 3.

European Search Report for Application No./Patent No. 18168869.8-1111, dated May 29, 2018, 6 pages.

European Search Report for Application No./Patent No. 19156603.3-1111, dated Mar. 22, 2019, 6 pages.

European Search Report for Application No./Patent No. 19168295.4-1111, dated Jul. 11, 2019, 6 pages.

European Search Report for Application No./Patent No. 19168301.0-1111, dated Jul. 19, 2019, 7 pages.

\* cited by examiner

DETERGENT COMPOSITION

REFERENCE TO A SEQUENCE LISTING

This application contains a Sequence Listing in computer readable form. The computer readable form is incorporated herein by reference.

FIELD OF THE INVENTION

The present invention relates to use of a detergent composition comprising a fatty acid-transforming enzyme to impart increased suds longevity in a washing process.

Preferably the use is in a manual washing process, i.e. for washing by hand, or in a non-fully automated washing machine, such as semi-automatic washing machine such as a twin-tub etc. Preferably the composition is a dishwashing detergent composition. Preferred compositions are in liquid form.

BACKGROUND OF THE INVENTION

Detergent compositions should have a good suds profile while providing good soil and grease cleaning. Users usually see foam as an indicator of the performance of the detergent composition. Moreover, the user of a detergent composition may also use the suds profile and the appearance of the foam (density, whiteness) as an indicator that the wash solution still contains active detergent ingredients. This is particularly the case for manual washing, also referred to herein as hand-washing, where the user usually doses the detergent composition depending on the suds remaining and renews the wash solution when the suds/foam subsides or when the foam does not look thick enough. Thus, a detergent composition, particularly a manual wash detergent composition that provides little or low density suds, or short-lived suds would tend to be replaced by the user more frequently than is necessary.

Thus, it is desirable for a detergent composition to provide good foam height and density as well as good foam duration during the initial mixing of the detergent with water and during the entire washing operation.

It has been found that some types of soil, in particular greasy soils, act as a foam suppressor, triggering consumers to replace the product more frequently than is necessary. As such there is a need to provide detergent compositions having good suds longevity even in the presence of oily or fatty soils such as vegetable oils including but not limited to olive oil, palm oil and/or coconut oil, and which at the same time provide good soil removal.

SUMMARY OF THE INVENTION

The present invention provides use of a detergent composition comprising a fatty acid-transforming enzyme to impart increased suds longevity in a washing process.

Preferably the detergent composition is a manual-washing composition. Preferably the detergent composition is for manual dishwashing. Preferably the detergent composition comprises a laundry washing composition, preferably for washing delicate fabrics. Preferred compositions are in the form of a liquid, optionally enclosed in a water soluble film in the form of a pouch, preferably a multi-compartment pouch, optionally with a particulate composition in at least one compartment.

The invention also provides a method of promoting suds longevity in a washing process for washing soiled articles, preferably dishware, comprising the step of: delivering a composition comprising a fatty acid-transforming enzyme to a volume of water to form a wash liquor and immersing the soiled articles, preferably dishware or fabric in the liquor, and optionally rinsing and drying the articles.

Preferably the composition also comprises a surfactant system.

The invention provides increased suds longevity, especially over time as soiled articles are cleaned.

DETAILED DESCRIPTION OF THE INVENTION

Definitions

As used herein, the articles "a" and "an" when used in a claim, are understood to mean one or more of what is claimed or described.

As used herein, the term "substantially free of" or "substantially free from" means that the indicated material is present in an amount of no more than about 5 wt %, preferably no more than about 2%, and more preferably no more than about 1 wt % by weight of the composition.

As used therein, the term "essentially free of" or "essentially free from" means that the indicated material is present in an amount of no more than about 0.1 wt % by weight of the composition, or preferably not present at an analytically detectible level in such composition. It may include compositions in which the indicated material is present only as an impurity of one or more of the materials deliberately added to such compositions.

As used herein the phrase "cleaning composition," "detergent composition," or "detergent or cleaning composition" are used interchangeably herein to refer to compositions and formulations designed for cleaning soiled articles. Such compositions include but are not limited to, dish-washing compositions, laundry detergent compositions, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, dish washing compositions, hard surface cleaning compositions, unit dose formulation, delayed delivery formulation, detergent contained on or in a porous substrate or nonwoven sheet, and other suitable forms that may be apparent to one skilled in the art in view of the teachings herein. Such compositions may be used as a pre-cleaning treatment, a post-cleaning treatment, or may be added during the rinse or wash cycle of the cleaning process. The cleaning compositions may have a form selected from liquid, powder, single-phase or multi-phase unit dose or pouch form, tablet, gel, paste, bar, or flake. In a preferred embodiment of the present invention, the cleaning composition of the present invention comprises a laundry or dish detergent composition, which is in a single phase or multiphase unit dose form as encapsulated by a single compartment or multi-compartment water-soluble pouch, e.g., formed by a water-soluble polymer such as polyvinyl alcohol (PVA) or copolymers thereof. Preferably the composition is for manual-washing. Preferably, the cleaning composition of the present invention is a dishwashing detergent. Preferably the composition is in the form of a liquid.

As used herein the term "increased suds longevity" means an increase in the duration of visible suds in a washing process cleaning soiled articles using the composition comprising fatty acid-transforming enzyme, compared with the suds longevity provided by the same composition and process in the absence of the fatty acid-transforming enzyme As used herein, the term "laundry detergent" means a liquid or solid composition, and includes, unless otherwise indicated, granular or powder-form all-purpose or "heavy-duty" washing agents, especially cleaning detergents as well as cleaning auxiliaries such as bleach additives or pre-treat types. In a preferred embodiment of the present invention, the laundry detergent is a liquid laundry detergent composition. Preferably the composition is for manual-washing. Preferably the cleaning composition is a laundry detergent composition preferably for cleaning delicate fabrics.

As used herein, the term "soiled articles" refers non-specifically to any article comprising flexible material consisting of a network of natural or artificial fibers, including natural, artificial, and synthetic fibers, such as, but not limited to, cotton, linen, wool, polyester, nylon, silk, acrylic, and the like, as well as various blends and combinations. Soiled articles may further refer to any article having hard surfaces, including natural, artificial, or synthetic surfaces, such as, but not limited to, tile, granite, grout, glass, composite, vinyl, hardwood, metal, cooking surfaces, plastic, and the like, as well as blends and combinations, and in particular, dishware.

As used herein, the term "water hardness" or "hardness" means uncomplexed cations ion (i.e., $Ca^{2+}$ or $Mg^{2+}$) present in water that have the potential to precipitate under alkaline conditions, and thereby diminishing the surfactancy and cleaning capacity of surfactants. Further, the terms "high water hardness" and "elevated water hardness" can be used interchangeably and are relative terms for the purposes of the present invention, and are intended to include, but not limited to, a hardness level containing at least 12 grams of calcium ion per gallon water (gpg, "American grain hardness" units).

Washing Process

According to the invention the washing process comprises mixing the composition comprising a fatty acid-transforming enzyme with water to form a wash liquor. This may be by adding the composition to water which the soiled articles are then immersed into, or by applying the detergent composition directly onto soiled articles, or onto a cleaning implement and using the cleaning implement to clean the soiled articles, with simultaneous or subsequent addition of water to form the wash liquor. When a cleaning implement is used, preferably the cleaning implement is a sponge and more preferably the sponge is wet so that the wash liquor is present on the implement. The washed articles are optionally rinsed and dried.

During the washing process greasy soils are removed from the soiled articles, for example oils used in cooking such as olive oil, palm oil and/or coconut oil and/or body soils such as sebum. The present invention has been found to have particularly efficacy in the presence of fatty acids or salts thereof. These may be present either in the soil or released to the wash liquor during removal of soils which break down to generate fatty acids.

Thus the use of the invention may comprise the step of applying the composition comprising fatty acid-transforming enzyme, preferably in liquid form, onto the soiled articles especially dishware, either in diluted or neat form and adding water and mixing to create suds, then rinsing and drying.

By "in its neat form", it is meant herein that said composition is applied directly onto the surface to be treated and/or onto a cleaning device or implement such as a pre-treat device, dish cloth, a sponge or a dish brush without undergoing any dilution (immediately) prior to the application. The cleaning device or implement is preferably wet before or after the composition is delivered to it. By "diluted form", it is meant herein that said composition is diluted by the user with an appropriate solvent, typically water. By "rinsing", it is meant herein contacting the surface, such as the dishware cleaned using a process according to the present invention with substantial quantities of appropriate solvent, typically water, after the step of applying the liquid composition herein onto said dishware. By "substantial quantities", it is meant usually about 1 to about 10 liters.

The composition herein can be applied in its diluted form. Soiled articles e.g. dishes are contacted with an effective amount, typically from about 0.5 ml to about 20 ml (per about 25 dishes being treated), preferably from about 3 ml to about 10 ml, of the detergent composition, preferably in liquid form, diluted in water. The actual amount of detergent composition used will be based on the judgment of user, and will typically depend upon factors such as the particular product formulation of the composition, including the concentration of active ingredients in the composition, the number of soiled articles to be cleaned, the degree of soiling on the soiled articles, and the like. Generally, particularly for dish-washing, from about 0.01 g to about 150 g, preferably from about 3 g to about 40 g of the detergent composition comprising the fatty acid-transforming enzyme, preferably a liquid composition, is combined with from about 2000 ml to about 20000 ml, more typically from about 5000 ml to about 15000 ml of water, more typically from about 5000 ml to about 15000 ml, to form a wash liquor. The soiled articles may then be immersed in the wash liquor, where contacting the soiled surface with a cloth, sponge, or similar article cleans them. The cloth, sponge, or similar article may be immersed in the detergent composition and water mixture prior to being contacted with the dish surface, and is typically contacted with the soiled surface for a period of time ranged from about 1 to about 20 minutes, or from 1 to 10 minutes, or especially for dishwashing, from 1 to 120 seconds, or 1 to 60 seconds although the actual time will vary with each application and user. The contacting of cloth, sponge, or similar article to the surface is preferably accompanied by a concurrent scrubbing of the surface.

Another method of the present invention will comprise immersing the soiled articles, such as dishes, into a water bath or held under running water without any detergent composition. A device for absorbing detergent composition, such as a sponge or pre-treat device, is placed directly into a separate quantity of undiluted detergent composition, preferably in the form of a liquid, for a period of time typically ranging from about 1 to about 5 seconds. The absorbing device, and consequently the undiluted detergent composition, is then contacted individually to the surface of each of the soiled articles to remove said soiling. The absorbing device is typically contacted with each surface for a period of time range from about 1 to about 10 seconds, although the actual time of application will be dependent upon factors such as the degree of soiling of the surface. The contacting of the absorbing device to the soiled surface is preferably accompanied by concurrent scrubbing.

Alternatively, the device may be immersed in a mixture of the detergent composition and water prior to being contacted with the soiled surface, the concentrated solution is made by diluting the detergent composition with water in a small container that can accommodate the cleaning device at weight ratios ranging from about 95:5 to about 5:95, preferably about 80:20 to about 20:80 and more preferably about 70:30 to about 30:70, respectively, of detergent composition, preferably in liquid form the ratio of detergent composition: water respectively depending upon the user habits and the cleaning task. These processes using a device are particularly applicable to soiled articles which are dishware.

The detergent composition according to the invention might also be used as a pretreating composition prior to exposing the soiled items to an automatic washing machine, particularly a semi-automatic washing machine. Following pretreatment, the soiled surface may be washed in a washing machine or otherwise rinsed. In machine methods soiled articles may be treated with an aqueous wash liquor in which an effective amount of a cleaning composition of the invention is dissolved or dispensed into therein. In particular for a laundry washing process an "effective amount" of the cleaning composition may mean from about 10 g to about 300 g of product dissolved or dispersed in a wash solution of volume from about 5 litres to about 65 litres. The water temperatures may range from about 5° C. to about 100° C. The water to soiled material (e.g., fabric) ratio may be from about 1:1 to about 30:1. The compositions may be employed at concentrations of from about 500 ppm to about 15,000 ppm in solution. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The present invention is particularly directed to use in a manual washing methods or hand washing/soak methods, and combined manual washing with semi-automatic washing machines, are also included. Temperatures are typically lower, below 50, 45, 40, 35, 30, or 25° C.

Fatty Acid-Transforming Enzyme

The fatty acid-transforming enzyme is preferably present in the composition in an amount from 0.00001 to 2 wt % based on the weight of the active protein. More preferably the fatty acid-transforming enzyme may be present in amounts from 0.0001 to 1 wt %, more preferably from 0.0005 to 0.5 wt % or 0.001 to 0.2 wt % based on active protein.

The fatty acid-transforming enzyme may be any enzyme which reacts with a fatty acid to break it down.

The fatty acid-transforming enzyme may be selected from E.C. classification numbers 1.11.2.3 (plant seed peroxygenase), 1.13.11.77 (oleate 10S lipoxygenase), 3.1.2.14 (oleoyl-[acyl-carrier-protein] hydrolase, 3.5.1.99 (fatty acid amide hydrolase), 4.2.1.53 (oleate hydratase), EC 1.2.99.6 (carboxylate reductase), EC 1.11.1.3 (fatty-acid peroxidase), E.C. 1.11.2.1 (unspecific peroxygenase), EC 1.11.2.4 (fatty-acid peroxygenase), EC 1.13.11.33 (arachidonate 15-lipoxygenase), EC 3.1.1.1 (carboxylesterase), EC 3.1.1.3 (triacylglycerol lipase), EC 3.1.1.4 and E.C. 3.1.1.5 (phospholipase A2 and lysophospholipase, respectively), EC 3.1.1.13 (sterol esterase), EC 3.1.1.23 (acylglycerol lipase), EC 3.1.1.26 (galactolipase), EC 3.1.1.32 (phospholipase A1), EC 3.1.1.50 (wax-ester hydrolase), EC 3.1.1.52 (phosphatidylinositol deacylase), EC 3.1.1.67 (fatty-acyl-ethyl-ester synthase), E.C. 3.1.1.74 (cutinase), EC 3.1.1.79 (hormone-sensitive lipase), EC 3.5.1.4 (amidase), EC 3.5.1.13 (aryl-acylamidase), EC 3.5.1.23 (ceramidase), EC 3.5.1.60 (N-(Long-chain-acyl)ethanolamine deacylase), EC 5.2.1.5 (linoleate isomerase), EC 5.3.3.B2 (linoleate (10E,12Z)-isomerase), EC 5.3.3.13 ((5Z,8Z,11Z,14Z,17Z)-eicosapentaenoate delta8,11-delta7,9-isomerase), decarboxylases and mixtures thereof.

Enzymes from the following classes are not preferred fatty acid-transforming enzymes useful herein: EC 1.2.1.42 (hexadecanal dehydrogenase (acylating)), EC 1.2.1.80 (long-chain acyl-[acyl-carrier-protein] reductase), EC 1.3.1.16 (beta-nitroacrylate reductase), EC 1.14.13.199 (docosahexaenoic acid omega-hydroxylase), EC 1.14.14.1 (unspecific monooxygenase), EC 1.14.15.3 (alkane 1-monooxygenase), EC 1.14.19.1 (stearoyl-CoA 9-desaturase), EC 1.14.19.3 (acyl-CoA 6-desaturase), EC 1.14.19.5 (acyl-CoA 11-(Z)-desaturase), EC 1.14.19.6 (DELTA12-fatty-acid desaturase), EC 1.14.19.39 (acyl-lipid Delta12-acetylenase), EC 2.1.1.15 (fatty-acid O-methyltransferase), EC 3.1.2.2 (palmitoyl-CoA hydrolase), EC 3.1.2.20 (acyl-CoA hydrolase), EC 3.5.1.70 (aculeacin-A deacylase), EC 4.2.1.92 (hydroperoxide dehydratase), EC 6.2.1.3 (long-chain-fatty-acid-CoA ligase), EC 6.2.1.20 (long-chain-fatty-acid-[acyl-carrier-protein] ligase).

Where necessary, the composition comprises, provides access to or forms in situ any additional substrate necessary for the effective functioning of the enzyme: hydroperoxide for plant seed peroxygenase; oxygen for oleate 10S lipoxygenase and/or Arachidonate 15-lipoxygenase; acyl carrier protein for oleoyl-[acyl-carrier-protein] hydrolase; ammonia or amines such as ethanolamine for fatty acid amide hydrolase and/or amidase; water for oleate hydratase; e.g. reduced viologens for carboxylate reductases; hydrogen peroxide for fatty-acid peroxidase, unspecific peroxygenase and/or fatty-acid peroxygenase; alcohol for carboxylesterase and/or cutinase; glycerol/mono/diglyceride for triacylglycerol lipase; phosphocholine for phospholipase A2 and/or lysophospholipase; sterol for sterol esterase; glycerol for acylglycerol lipase; galactosyl glycerol for galactolipase; glycero-3-phosphocholine for phospholipase A1; long chain alcohol for wax-ester hydrolase; 1-acylglycerophosphoinositol for phosphatidylinositol deacylase; ethanol for fatty-acyl-ethyl-ester synthase; glycerol/mono/diglyceride for hormone-sensitive lipase; aniline for aryl acylamidase; sphingosine-type amines for ceramidase; and ethanolamine for N-(Long-chain-acyl)ethanolamine deacylase.

Preferred fatty acid-transforming enzymes include lipoxygenases, peroxygenases, fatty acid decarboxylases and oleate hydratases.

A particularly preferred class of fatty acid-transforming enzymes is oleic acid-transforming enzymes. The oleic acid-transforming enzyme transforms oleic acid and/or salts thereof.

Preferably the fatty acid-transforming enzyme is an oleate hydratase from class EC 4.2.1.53. Suitable oleate hydratases include the wild-types oleate hydratases listed in Table 1 and variants thereof which exhibit oleate hydratase activity. Preferred oleate hydratases exhibit over 20, 30, 40, 50, 60, 70, 80, 90, 95, or 98% identity to one of more of the wild types oleate hydratases listed in Table 1.

TABLE 1

| Origin | SEQ ID |
|---|---|
| *Elizabethkingia meningoseptica* | 1 |
| *Lysinibacillus fusiformis* | 2 |
| *Macrococcus caseolyticus* | 3 |
| *Lactobacillus acidophilus* | 4 |
| *Stenotrophomonas maltophilia* | 5 |
| *Streptococcus pyogenes* | 6 |
| *Bifidobacterium breve* | 7 |
| *Bifidobacterium animalis* subsp. *lactis* (strain BB-12) | 8 |
| *Lactobacillus plantarum* subsp. *plantarum* ST-III | 9 |
| *Lactobacillus rhamnosus* LGG | 10 |

TABLE 1-continued

| Origin | SEQ ID |
|---|---|
| *Lactobacillus casei* W56 | 11 |
| *Lactobacillus delbrueckii* subsp. *bulgaricus* | 12 |

A further class of fatty acid transforming enzymes are fatty acid decarboxylases. The term "fatty acid decarboxylase" or "a polypeptide having fatty acid decarboxylase activity" means an enzyme capable of catalyzing the elimination of the carboxyl group of a fatty acid. For the purposes of the present invention, fatty acid decarboxylase activity is defined by an enzyme or enzyme/cofactor/co-substrate system capable of catalyzing the conversion of any C10-20 saturated, monounsaturated or polyunsaturated fatty acid into its corresponding terminal alkene as shown in Scheme 1.

Scheme 1

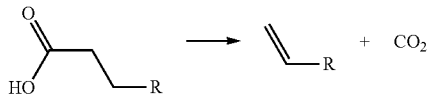

Suitable enzymes may be found in Cytochrome P450 families, although only a very small subset of Cytochrome P450 enzymes exhibit this activity. One example is the OleT$_{JE}$ enzyme endogenous to *Jeotgalicoccus* sp. 8456, and its variants. OleT$_{JE}$ binds strongly to a range of long chain fatty acids, and produces terminal alkenes from a wide variety of saturated fatty acids, using hydrogen peroxide as co-substrate. The amino acid sequence of OleT$_{JE}$ and its properties are given in J. Belcher et al., *J. Biol. Chem.* (2014), 289, 10: 6535-6550. Variants of the enzyme with fused domains are capable of using molecular oxygen as co-substrate in the presence of an additional cofactor, as described by Y. Liu et al., *Biotechnol. Biofuels* (2014) 7: 28. OleT$_{JE}$ is a member of the Cytochrome P450 family CYP152 and is classified as CYP152L1. Related Cytochrome P450 enzymes may exhibit significant decarboxylase activity in line with OleT$_{JE}$ in wild-type form, yet others such as CYP152A1 and CYP152B1 are described as being more effective at catalyzing beta hydroxylation of fatty acids although protein engineering has been proven to convert such enzymes into more effective fatty acid decarboxylases, for example by making the Gln85His substitution in CYP152A1. Other suitable fatty acid decarboxylase enzymes are nonheme iron oxidase enzymes such as the UndA enzyme endogenous to *Pseudomonas* sp., as described by Z. Rui et al., *PNAS*, (2014), 111, 18237-18242. This is a member of the TENA/THI-4 protein family Preferred fatty acid transforming enzymes are active on unsaturated fatty acids having 10 to 20 carbon atoms, particularly oleic acid.

The fatty-acid transforming enzyme may be incorporated into the detergent composition via an additive particle, such as an enzyme granule or in the form of an encapsulate, or may be added in the form of a liquid formulation.

Suitable enzyme granules include: (i) spray-dried particles, (ii) layered particles in which the enzyme is coated as a layer around a pre-formed inert core, and fluid bed apparatus is used to adhere layers of coating material from aqueous solution containing coating materials; (iii) particles in which enzyme is absorbed into a core, (iv) extruded or pelletized enzyme particles in which an enzyme-containing paste is pressed into pellets or under pressure is extruded through orifices and cut into particles prior to drying; (v) prilled products in which an enzyme powder is suspended in molten wax and the suspension sprayed into a cooling chamber (e.g. through a rotating disc atomiser), (vi) agglomerated enzyme particles prepared by a process in which an enzyme-containing liquid is added to a dry powder composition comprising conventional granulating materials which may include e.g. fillers and binders optionally mixed with filaments such as cellulose fibres, or polymeric filaments such as polyvinyl pyrrolidone or polyvinyl alcohol filaments, to give extra strength and reduce dusting. These may be particularly preferred when the detergent composition is particulate, or for suspension in a liquid.

In particular when the cleaning composition comprises a liquid, it may be preferred to incorporate the enzyme via an encapsulate. Encapsulating the enzyme promotes the stability of the enzyme in the composition and helps to counteract the effect of any hostile compounds present in the composition, such as bleach, protease, surfactant, chelant, etc.

When in encapsulated form the enzyme is typically encapsulated in a polymeric material. Methods of encapsulation of the enzymes are for example, by spray-drying a liquid composition containing the enzyme(s) and the polymer(s), or by drying a liquid composition containing the enzyme and polymer, or by emulsion polymerisation, co-acervation, precipitation or interfacial polymerisation optionally in the presence of the enzyme, optionally followed by drying and/or size reduction processes. Suitable polymers for encapsulating enzymes include optionally modified: polyvinyl alcohol, polyvinylpyrrolidone, carboxymethylcellulose, guar gum, polycarboxylic acid, methylcellulose, hydroxypropyl methylcellulose, proteins, polybranched polyamines, such as polyethyleneimines (PEI), (hydrophobically modified) polysaccharide, a cellulosic polymer selected from the group consisting of, and mixtures thereof and derivatives or co-polymers thereof. Examples of modified cellulosic polymers include those mentioned above and in addition, hydroxypropyl methylcellulose phthalate, cellulose acetate phthalate Examples of modified gums include modified guar gum, gum benzoin, gum tragacanth, gum arabic and gum acacia. Examples of modified proteins are modified casein, gelatin and albumin. Examples of modified polymers may be selected from copolymers of at least one hydrophobic vinylic monomer with a least one hydrophilic vinylic monomer. Suitable hydrophilic vinylic monomer is vinylpyrrolidone. Suitable hydrophobic vinylic monomer is C1-C18 alkyl acrylates, C1-C18 alkyl methacrylates, C3-C18 cycloalkyl acrylates, C3-C18 cycloalkyl methacrylates and vinyl C1-C18 alkanoates and mixtures thereof. The polymer may comprise a polymer selected from homo- and copolymers having a C—C-backbone, wherein the C—C-backbone carries carboxylgroups, which may be present in the acidic form or in the neutralized form, and wherein the C—C-backbone comprises at least 20% by weight, e.g. from 20 to 98% by weight, based on the total weight of the polymer (i.e. based on the total weight of repeating units in the polymer P), of hydrophobic repeating units. The polymer may comprise branching, for example branched copolymer matrix particles formed from vinyl pyrrolidone and vinyl acetate. The polymer may comprise a copolymers, for example as described in WO2010/003934, based on maleic acid or (meth)acrylic acid. The polymer may be cross-linked.

Preferred polymers have a molecular weight from 1000 to 500,000, or 2000 to 200000 Dalton weight average. Typically the weight ratio of enzyme to polymer is from 1:50 to 10:1. The polymer may be selected to be substantially soluble in an aqueous solution having an ionic strength of 0 mol/kg and insoluble in an aqueous solution having an ionic strength of more than 1 mol/kg according to method 1, for example as described in WO2008/084093, for example in which the polymer comprises 35-95% w/w of hydrophilic monomer units, based on the total weight of the polymer.

Hydrophobically modified polyvinyl alcohol or hydrophobically modified polyvinyl pyrrolidone may be preferred, optionally with high levels of hydrolysis, greater than 60%, or even greater than 80 or 90%. Suitable hydrophobic modifying groups include keto-ester and/or butyryl groups and mixtures thereof and preferably the total degree of substitution (DS) is between about 3% and 20%.

The fatty acid transforming enzyme, when present in an additive particle may be the only enzyme in the additive particle or may be present in the additive particle in combination with one or more additional enzymes.

Suitable additional enzymes include protease such as metalloprotease or alkaline serine protease, such as subtilisin, amylase, lipase, cellulase, mannanase, pectinase, DNAse, oxidoreductase, peroxidases, lipases, phospholipases, cellobiohydrolases, cellobiose dehydrogenases, esterases, cutinases, pectinases, pectate lyases, keratinases, reductases, oxidases, phenoloxidases, lipoxygenases, ligninases, pullulanases, tannases, pentosanases, glucanases, arabinosidases, hyaluronidase, chondroitinase, laccases, amylases, and mixtures thereof. In a preferred embodiment, the fatty acid transforming enzyme, preferably selected from oleate hydratase, fatty acid lipoxygenase and fatty acid decarboxylase, more preferably oleate hydratase, may be incorporated into an additive particle in combination with an amylase, cellulase, protease and/or lipase enzyme, preferably a lipase or protease enzyme.

Surfactant System

The detergent composition typically comprises from about 1% to about 60%, preferably from about 5% to about 50% more preferably from about 8% to about 45% by weight thereof of a surfactant system. The surfactant system comprises one or more surfactants selected from the group consisting of anionic surfactants, cationic surfactants, non-ionic surfactants, amphoteric surfactants, zwitterionic surfactants, and mixtures thereof. Preferably, the surfactants comprise an anionic surfactant selected from the group consisting of alkyl benzene sulfonate, alkoxylated alkyl sulfates, alkyl sulfates, and mixtures thereof.

A preferred surfactant system for providing food cleaning and good suds profile comprises i) an anionic surfactant; and ii) an amphoteric and/or zwitterionic surfactant. Preferably the weight ratio of anionic surfactant to amphoteric and/or zwitterionic surfactant is less than 9:1, more preferably less than 5:1 to about 1:2, more preferably from about 4:1 to about 1:1 and especially from about 4:1 to about 2:1

Extremely useful surfactant systems for use herein include those comprising anionic surfactants and comprising in addition, amine oxide and/or betaine surfactants. Amine oxide surfactants are particularly preferred. Preferably the surfactant system comprises an anionic surfactant selected from alkyl sulphate, alkyl alkoxy sulphate especially alkyl ethoxy sulphate, and mixtures thereof, in combination with amine oxide, most preferably in a weight % ratio of less than 9:1, more preferably less than 5:1 to about 1:2, more preferably from about 4:1 to about 1:1 and especially from about 4:1 to about 2:1.

Another preferred surfactant system for use herein comprises an anionic and amphoteric/zwitterionic system in which the amphoteric to zwitterionic weight ratio is preferably from about 2:1 to about 1:2. In particular a system in which the amphoteric surfactant comprises an amine oxide surfactant and the zwitteronic surfactant comprises a betaine. Preferred ratios of amine oxide to betaine are from 1.5:1 to 1:1.5, preferably from 1.2:1 to 1:1.2, most preferably about 1:1.

Also preferred for use herein are surfactant systems comprising non-ionic surfactants. Especially preferred surfactant systems for the composition of the invention comprise an anionic surfactant preferably selected from the group consisting of alkyl sulphate, alkyl alkoxy sulphate and mixtures thereof, more preferably an alkoxylated sulfate. Preferred surfactant systems comprise in addition an amphoteric surfactant, preferably an amine oxide surfactant. Preferred surfactant systems comprise a non-ionic surfactant. In summary, the most preferred surfactant system for use herein comprises an alkoxylated sulfate surfactant, amine oxide and non-ionic surfactant. Most preferably the nonionic surfactant is an alkoxylated alcohol surfactant, especially an ethoxylated alcohol surfactant.

Anionic Surfactant

Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate so as to form a water-soluble compound. Usually, the hydrophobic group will comprise a C 8-C 22 alkyl, and/or acyl group. Such surfactants are employed in the form of water-soluble salts and the salt-forming cation usually is selected from sodium, potassium, ammonium, magnesium and mono-, di- or tri-C 2-C 3 alkanolammonium, with the sodium, cation being the usual one chosen.

Preferably the surfactant system comprises an anionic surfactant or mixtures thereof. The anionic surfactant comprises any anionic cleaning surfactant, preferably selected from anionic sulphate or sulphonate surfactants or mixtures thereof.

Preferably the anionic surfactant is an alkoxylated alkyl sulphate surfactant, preferably an ethoxylated alkyl sulphate surfactant, preferably having an average ethoxylation degree of from about 0.2 to about 3, more preferably from about 0.3 to about 2, even more preferably from about 0.4 to about 1.5, and especially from about 0.4 to about 1. When the anionic surfactant is a mixture of surfactants, the alkoxylation degree is the weight average alkoxylation degree of all the components of the mixture (weight average alkoxylation degree). In the weight average alkoxylation degree calculation the weight of anionic surfactant components not having alkoxylated groups should also be included.

Weight average alkoxylation degree=
($x1$*alkoxylation degree of surfactant
$1$+$x2$*alkoxylation degree of surfactant
$2$+ . . . )/($x1$+$x2$+ . . . )

wherein $x1$, $x2$, . . . are the weights in grams of each anionic surfactant of the mixture and alkoxylation degree is the number of alkoxy groups in each anionic surfactant.

Also preferred are branched anionic surfactants, typically having a weight average level of branching of from 2 to 60% by weight, particularly those having a weight average level of branching of from about 5% to about 40%.

Preferably the anionic surfactant to be used in the detergent of the present invention comprises a branched anionic surfactant having a level of branching of from about 5% to about 40%, preferably from about 10 to about 35% and more preferably from about 20% to about 30%. Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the anionic surfactant used in the detergent of the invention. Most preferably the branched anionic surfactant is selected from alkyl sulphates, alkyl ethoxy sulphates, and mixtures thereof.

The branched anionic surfactant can be a single anionic surfactant or a mixture of anionic surfactants. In the case of a single surfactant the percentage of branching refers to the weight percentage of the hydrocarbyl chains that are branched in the original alcohol from which the surfactant is derived.

In the case of a surfactant mixture the percentage of branching is the weight average and it is defined according to the following formula:

Weight average of branching(%)=[($x1$*wt % branched alcohol 1 in alcohol 1+$x2$*wt % branched alcohol 2 in alcohol 2+ . . . )/($x1$+$x2$+ . . . )]*100 wherein $x1$, $x2$, . . . are the weight in grams of each alcohol in the total alcohol mixture of the alcohols which were used as starting material for the anionic surfactant for the detergent of the invention. In the weight average branching degree calculation the weight of anionic surfactant components not having branched groups should also be included. It may be preferred that the surfactant system comprises at least 50%, more preferably at least 60% and preferably at least 70% of branched anionic surfactant by weight of the surfactant system. In a particularly preferred surfactant system, the branched anionic surfactant comprises more than 50% by weight thereof of an alkyl ethoxylated sulphate having an ethoxylation degree of from about 0.1 to 5 or 0.2 to about 3 and preferably a level of branching of from about 5% to about 40%.

Preferably, the branched anionic surfactant comprises at least 50%, more preferably at least 60% and especially at least 70% of a sulphate surfactant by weight of the branched anionic surfactant. Especially preferred detergents from a cleaning view point art those in which the branched anionic surfactant comprises more than 50%, more preferably at least 60% and especially at least 70% by weight thereof of sulphate surfactant and the sulphate surfactant is selected from the group consisting of alkyl sulphate, alkyl ethoxy sulphates and mixtures thereof. Even more preferred are those in which the branched anionic surfactant has a degree of ethoxylation of from about 0.2 to about 3, more preferably from about 0.3 to about 2, even more preferably from about 0.4 to about 1.5, and especially from about 0.4 to about 1 and even more preferably when the anionic surfactant has a level of branching of from about 10% to about 35%, more preferably from about 20% to 30%.

Sulphate Surfactants

Preferably the surfactant comprises anionic sulphate surfactants. Anionic sulphate surfactants selected from the group consisting of alkyl sulphate, alkyl alkoxy sulphate and mixtures thereof may be particularly preferred, especially for dishwashing compositions.

Especially preferred are alkoxylated anionic surfactants, more preferably alkyl alkoxy sulphate surfactant. Preferred alkyl alkoxyl sulphates for use herein are alkyl ethoxy sulphates. Suitable sulphate surfactants for use herein include water-soluble salts of C8-C18 alkyl or hydroxyalkyl, sulphate and/or ether sulfate. Suitable counterions include alkali metal cation or ammonium or substituted ammonium, but preferably sodium.

The sulphate surfactants may be selected from C8-C18 primary, branched chain and random alkyl sulphates (AS); C8-C18 secondary (2,3) alkyl sulphates; C8-C18 alkyl alkoxy sulphates (AExS) wherein preferably x is from 1-30 in which the alkoxy group could be selected from ethoxy, propoxy, butoxy or even higher alkoxy groups and mixtures thereof. The alkoxylated anionic surfactant typically has an average alkoxylation degree of from about 0.1 to 11 or 0.1 to 7, preferably from about 0.2 to about 4, even more preferably from about 0.3 to about 3, even more preferably from about 0.4 to about 1.5 and especially from about 0.4 or 0.2 to about 1. Preferably, the alkoxy group is ethoxy.

Alkyl sulfates and alkyl alkoxy sulfates are commercially available with a variety of chain lengths, ethoxylation and branching degrees. Commercially available sulphates include, those based on Neodol alcohols ex the Shell company, Lial—Isalchem and Safol ex the Sasol company, natural alcohols ex The Procter & Gamble Chemicals company.

Preferably, the surfactant system comprises alkyl sulfates and/or alkyl ethoxy sulfates; more preferably a combination of alkyl sulfates and/or alkyl ethoxy sulfates with a combined average ethoxylation degree of less than 5, preferably less than 3, more preferably less than 2 and more than 0.5. Preferably the anionic surfactant has an average level of branching of from about 5% to about 40%.

Sulphonate Surfactants

Suitable sulphonate surfactants for use herein include water-soluble salts of C8-C18 alkyl or hydroxyalkyl sulphonates; C11-C18 alkyl benzene sulphonates (LAS), modified alkylbenzene sulphonate (MLAS) as discussed in WO 99/05243, WO 99/05242, WO 99/05244, WO 99/05082, WO 99/05084, WO 99/05241, WO 99/07656, WO 00/23549, and WO 00/23548; methyl ester sulphonate (MES); and alpha-olefin sulphonate (AOS). Those also include the paraffin sulphonates may be monosulphonates and/or disulphonates, obtained by sulphonating paraffins of 10 to 20 carbon atoms. The sulfonate surfactant also include the alkyl glyceryl sulphonate surfactants. In particular, for a laundry detergent the anionic surfactant preferably comprises at least 40% or more preferably at least 50% or at least 60% or even at least 80 or 90% sulphonate surfactant.

Fatty Acids

Water-soluble salts of the higher fatty acids, i.e., "soaps", may also be useful anionic surfactants in the cleaning compositions of the present invention, particularly for laundry detergents. However, the cleaning compositions of the present invention preferably contains soaps at a relatively low level, e.g., no more than about 3 wt %, more preferably not more than about 2 wt % or 1 wt %, and most preferably said cleaning composition is essentially free of soaps. Where fatty acids are added, they preferably contain very low levels of oleic acid. Levels of oleic acid in the composition are preferably below 0.5, more preferably below 0.3, more preferably below 0.2 or even below 0.1 wt % of the compositions, most preferably essentially free of oleic acid. Higher levels may be accommodated, however, additional enzyme may need to be present to counteract the competition caused by their presence. Where oleic acid is incorporated, it may be preferred to also incorporate enzyme stabilizer. Physical stabilization may be for example by encapsulation may be particularly preferred, such encapsulation providing a physical stabilizer.

Non-Ionic Surfactant

Nonionic surfactant, when present, are typically present in an amount of from 0.05% to 30%, preferably 0.1% to 20%, most preferably 0.5% to 10% or 0.5% to 7% or even 0.5% to 3% by weight of the composition. The nonionic surfactant is preferably present in the surfactant system in amounts from 1 to 60 wt % of the surfactant system, and particularly for laundry detergents preferably from 2 to 60, or 5 to 55 wt % based on the surfactant system. Suitable nonionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol. Highly preferred nonionic surfactants are the condensation products of Guerbet alcohols with from 2 to 18 moles, preferably 2 to 15, more preferably 5-12 of ethylene oxide per mole of alcohol.

However, in certain preferred embodiments of the present invention, particularly for dishwashing the cleaning composition contains nonionic surfactants at a relatively low level, e.g., no more than about 3 wt %, more preferably not more than about 2 wt % or 1 wt %, and most preferably said cleaning composition is essentially free of nonionic surfactants.

Other surfactants useful herein include amphoteric surfactants, zwitterionic surfactants and cationic surfactants. Such surfactants are typically present at levels from about 0.2 wt %, 0.5 wt % or 1 wt % to about 10 wt %, 20 wt % or 30 wt %. Preferably, the composition of the present invention will further comprise amphoteric and/or zwitterionic surfactant, more preferably an amine oxide and/or betaine surfactant, most preferably an amine oxide.

In a preferred but not necessary embodiment of the present invention, the cleaning composition is a liquid dish detergent composition containing from about 0.5 wt % to about 20 wt % of one or more amphoteric and/or zwitterionic surfactants, preferably amine oxide.

Amphoteric Surfactant

Preferred amphoteric surfactants are selected from the group consisting of amine oxide surfactants, such as, for example, alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one R1 C8-18 alkyl moiety and 2 R2 and R3 moieties selected from the group consisting of C1-3 alkyl groups and C1-3 hydroxyalkyl groups. Preferably amine oxide is characterized by the formula R1-N(R2)(R3) O wherein R1 is a C8-18 alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides. Preferred amine oxides include linear C10, linear C10-C12, and linear C12-C14 alkyl dimethyl amine oxides. As used herein "mid-branched" means that the amine oxide has one alkyl moiety having n1 carbon atoms with one alkyl branch on the alkyl moiety having n2 carbon atoms. The alkyl branch is located on the α carbon from the nitrogen on the alkyl moiety. This type of branching for the amine oxide is also known in the art as an internal amine oxide. The total sum of n1 and n2 is from 10 to 24 carbon atoms, preferably from 12 to 20, and more preferably from 10 to 16. The number of carbon atoms for the one alkyl moiety (n1) should be approximately the same number of carbon atoms as the one alkyl branch (n2) such that the one alkyl moiety and the one alkyl branch are symmetric. As used herein "symmetric" means that |n1−n2| is less than or equal to 5, preferably 4, most preferably from 0 to 4 carbon atoms in at least 50 wt %, more preferably at least 75 wt % to 100 wt % of the mid-branched amine oxides for use herein. The amine oxide further comprises two moieties independently selected from a C1-3 alkyl, a C1-3 hydroxyalkyl group, or a polyethylene oxide group containing an average of from about 1 to about 3 ethylene oxide groups. Preferably the two moieties are selected from a C1-3 alkyl, more preferably both are selected as a C1 alkyl. Most preferably the amine oxide is alkyl dimethyl amine oxide, especially C10-C18 alkyl dimethyl amine oxide.

Zwitterionic Surfactant

Other suitable surfactants include betaines, such as alkyl betaines, alkylamidobetaines, amidazoliniumbetaines, sulfobetaines (also referred to as INCI sultaines) as well as the phosphobetaines. Preferred betaines meet formula I:

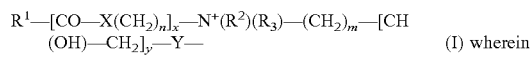

(I) wherein $R^1$ is a saturated or unsaturated C6-22 alkyl residue, preferably C8-18 alkyl residue, in particular a saturated C10-16 alkyl residue, for example a saturated C12-14 alkyl residue;

X is NH, $NR^4$ with C1-4 Alkyl residue $R^4$, O or S, n a number from 1 to 10, preferably 2 to 5, in particular 3, x 0 or 1, preferably 1, $R^2$, $R^3$ are independently a C1-4 alkyl residue, potentially hydroxy substituted such as a hydroxyethyl, preferably a methyl.

m a number from 1 to 4, in particular 1, 2 or 3, y 0 or 1 and

Y is COO, SO3, $OPO(OR^5)O$ or $P(O)(OR^5)O$, whereby $R^5$ is a hydrogen atom H or a C1-4 alkyl residue.

Preferred betaines are the alkyl betaines of the formula (Ia), the alkyl amido propyl betaine of the formula (Ib), the sulfo betaines of the formula (Ic) and the amido sulfobetaines of the formula (Id);

(Ia)

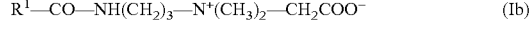
(Ib)

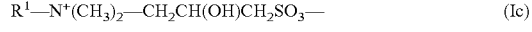
(Ic)

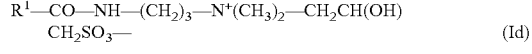
(Id)

in which $R^1$1 as the same meaning as in formula I. Particularly preferred betaines are the carbobetaines [wherein $Y^−$=$COO^−$], in particular the carbobetaines of the formula (Ia) and (Ib), more preferred are the alkylamidobetaines of the formula (Ib).

Examples of suitable betaines and sulfobetaines are the following [designated in accordance with INCH: almondamidopropyl of betaines, apricotam idopropyl betaines, avocadamidopropyl of betaines, babassuamidopropyl of betaines, behenam idopropyl betaines, behenyl of betaines, betaines, canolam idopropyl betaines, capryl/capram idopropyl betaines, carnitine, cetyl of betaines, cocamidoethyl of betaines, cocam idopropyl betaines, cocam idopropyl hydroxysultaine, coco betaines, coco hydroxysultaine, coco/oleam idopropyl betaines, coco sultaine, decyl of betaines, dihydroxyethyl oleyl glycinate, dihydroxyethyl soy glycinate, dihydroxyethyl stearyl glycinate, dihydroxyethyl tallow glycinate, dimethicone propyl of PG-betaines, erucam idopropyl hydroxysultaine, hydrogenated tallow of betaines, isostearam idopropyl betaines, lauram idopropyl betaines, lauryl of betaines, lauryl hydroxysultaine, lauryl sultaine, milkam idopropyl betaines, minkamidopropyl of betaines, myristam idopropyl betaines, myristyl of betaines, oleam idopropyl betaines, oleam idopropyl hydroxysultaine, oleyl of betaines, olivamidopropyl of betaines, palmam idopropyl betaines, palm itam idopropyl betaines, palmitoyl Carnitine, palm kernelam idopropyl betaines, polytetrafluoroethylene acetoxypropyl of betaines, ricinoleam idopropyl betaines, sesam idopropyl betaines, soyam idopropyl betaines, stearam idopropyl betaines, stearyl of betaines, tallowam idopropyl betaines, tallowam idopropyl hydroxysultaine, tallow of betaines, tallow dihydroxyethyl of betaines, undecylenam idopropyl betaines and wheat germam idopropyl betaines. A preferred betaine is, for example, cocoamidopropylbetaine.

The most preferred surfactant system particularly for a dishwashing detergent composition of the present invention comprises: (i) 1% to 40%, preferably 6% to 32%, more preferably 8% to 25% weight of the total composition of an anionic surfactant, preferably comprising an alkoxylated sulfate surfactant (ii) 0.01% to 20% wt, preferably from 0.2% to 15% wt, more preferably from 0.5% to 10% by weight of the composition of amphoteric and/or zwitterionic and/or nonionic surfactant. Preferred compositions comprise 0.01% to 20 wt % of the composition of amphoteric and nonionic surfactant, most preferably wherein the amphoteric surfactant comprises amine oxide surfactant. It has been found that such surfactant system in combination with the oleate hydratase enzyme will provide the excellent cleaning required from a manual dishwashing detergent while having very good suds profile, especially in the presence of greasy soils and break-down products of greasy soils, and provides a good finish of the washed items.

Enzyme Stabilizer

Preferably the composition of the invention comprises an enzyme stabilizer. Suitable enzyme stabilizers may be selected from chemical stabilizers for example from the group consisting of (a) univalent, bivalent and/or trivalent cations preferably selected from the group of inorganic or organic salts of alkaline earth metals, alkali metals, aluminum, iron, copper and zinc, preferably alkali metals and alkaline earth metals, preferably alkali metal and alkaline earth metal salts with halides, sulfates, sulfites, carbonates, hydrogencarbonates, nitrates, nitrites, phosphates, formates, acetates, propionates, citrates, maleates, tartrates, succinates, oxalates, lactates, and mixtures thereof. In a preferred embodiment the salt is selected from the group consisting of sodium chloride, calcium chloride, potassium chloride, sodium sulfate, potassium sulfate, sodium acetate, potassium acetate, sodium formate, potassium formate, calcium lactate, calcium nitrate and mixtures thereof. Most preferred are salts selected from the group consisting of calcium chloride, potassium chloride, potassium sulfate, sodium acetate, potassium acetate, sodium formate, potassium formate, calcium lactate, calcium nitrate, and mixtures thereof, and in particular potassium salts selected from the group of potassium chloride, potassium sulfate, potassium acetate, potassium formate, potassium propionate, potassium lactate and mixtures thereof. Most preferred are potassium acetate and potassium chloride. Preferred calcium salts are calcium formate, calcium lactate and calcium nitrate including calcium nitrate tetrahydrate. Calcium and sodium formate salts may be preferred. These cations are present at at least about 0.01 wt %, preferably at least about 0.03 wt %, more preferably at least about 0.05 wt %, most preferably at least about 0.25 wt % up to about 2 wt % or even up to about 1 wt % by weight of the total composition. These salts are formulated from about 0.1 to about 5 wt %, preferably from about 0.2 to about 4 wt %, more preferably from about 0.3 to about 3 wt %, most preferably from about 0.5 to about 2 wt % relative to the total weight of the composition. Further enzyme stabilizers can be selected from the group (b) carbohydrates selected from the group consisting of oligosaccharides, polysaccharides and mixtures thereof, such as a monosaccharide glycerate as described in WO201219844; (c) mass efficient reversible protease inhibitors selected from the group consisting of phenyl boronic acid and derivatives thereof, preferably 4-formyl phenylboronic acid; (d) alcohols such as 1,2-propane diol, propylene glycol; (e) peptide aldehyde stabilizers such as tripeptide aldehydes such as Cbz-Gly-Ala-Tyr-H, or disubstituted alaninamide; (f) carboxylic acids such as phenyl alkyl dicarboxylic acid as described in WO2012/19849 or multiply substituted benzyl carboxylic acid comprising a carboxyl group on at least two carbon atoms of the benzyl radical such as described in WO2012/19848, phthaloyl glutamine acid, phthaloyl asparagine acid, aminophthalic acid and/or an oligoamino-biphenyl-oligocarboxylic acid; and; (g) mixtures thereof. An example of a suitable mixture comprises: (1) reversible protease inhibitors such as a boron containing compound; (2) 1-2 propane diol; (3) calcium formate and/or sodium formate; and (4) any combination thereof.

If the cleaning composition of the present invention is provided in a powder form, it may also be especially preferred for the powder to comprise low levels, or even be essentially free, of builder. The term "essentially free" means that the composition "comprises no deliberately added" amount of that ingredient. In a preferred embodiment, the cleaning composition of the present invention comprises no builder.

Additional Enzymes

Suitable additional enzymes include protease such as metalloprotease or alkaline serine protease, such as subtilisin, amylase, lipase, cellulase, mannanase, pectinase, DNAse, oxidoreductase, peroxidases, lipases, phospholipases, cellobiohydrolases, cellobiose dehydrogenases, esterases, cutinases, pectinases, pectate lyases, keratinases, reductases, oxidases, phenoloxidases, lipoxygenases, ligninases, pullulanases, tannases, pentosanases, glucanases, arabinosidases, hyaluronidase, chondroitinase, laccases, amylases, and mixtures thereof.

Preferred compositions of the invention comprise one or more enzymes selected from lipases, proteases, cellulases, amylases and any combination thereof.

Each additional enzyme is typically present in an amount from 0.0001 to 1 wt % (weight of active protein) more preferably from 0.0005 to 0.5 wt %, most preferably 0.005-0.1%). It may be particularly preferred for the compositions of the present invention to additionally comprise a lipase enzyme. Lipases break down fatty ester soils into fatty acids which are then acted upon by the fatty acid-transforming enzyme into suds neutral or suds boosting agents. Suitable lipases include those of bacterial, fungal or synthetic origin, and variants thereof. Chemically modified or protein engineered mutants are also suitable. Examples of suitable lipases include lipases from *Humicola* (synonym *Thermomyces*), e.g., from *H. lanuginosa* (*T. lanuginosus*).

The lipase may be a "first cycle lipase", e.g. such as those described in WO06/090335 and WO13/116261. In one aspect, the lipase is a first-wash lipase, preferably a variant of the wild-type lipase from *Thermomyces lanuginosus* comprising T231R and/or N233R mutations. Preferred lipases include those sold under the tradenames Lipex®, Lipolex® and Lipoclean® by Novozymes, Bagsvaerd, Denmark.

Other suitable lipases include: Liprl 139, e.g. as described in WO2013/171241; and TfuLip2, e.g. as described in WO2011/084412 and WO2013/033318.

It may be particularly preferred for the compositions of the present invention to additionally comprise a protease enzyme. Since oleic acid and other foam suppressing fatty acids are present in body soils or even human skin, as protease enzyme acts as a skin care agent, or breaks down proteinaceous soils, fatty acids released are broken down, preventing suds suppression. Suitable proteases include metalloproteases and/or serine proteases. Examples of suitable neutral or alkaline proteases include: subtilisins (EC 3.4.21.62); trypsin-type or chymotrypsin-type proteases; and metalloproteases. The suitable proteases include chemically or genetically modified mutants of the aforementioned suitable proteases.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Preferenz P® series of proteases including Preferenz® P280, Preferenz® P281, Preferenz® P2018-C, Preferenz® P2081-WE, Preferenz® P2082-EE and Preferenz® P2083-A/J, Properase®, Purafect®, Purafect Prime®, Purafect Ox®, FN3®, FN4®, Excellase® and Purafect OXP® by DuPont, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (*Bacillus alkalophilus* subtilisin with mutations A230V+S256G+S259N) from Kao.

A suitable protease is described in WO11/140316 and WO11/072117.

It may be particularly preferred for the compositions of the present invention to additionally comprise an amylase enzyme. Since oily soils are commonly entrapped in starchy soils, the amylase and the fatty acid transforming enzymes work synergistically together: fatty acid soils are released by breakdown of starchy soils with amylase, thus, the fatty acid transforming enzyme is particularly effective in ensuring there is no negative impact on suds in the wash liquor. Preferred amylases are derived from AA560 alpha amylase endogenous to *Bacillus* sp. DSM 12649, preferably having the following mutations: R118K, D183*, G184*, N195F, R320K, and/or R458K. Suitable commercially available amylases include Stainzyme®, Stainzyme® Plus, Natalase, Termamyl®, Termamyl® Ultra, Liquezyme® SZ, Duramyl®, Everest® (all Novozymes) and Spezyme® AA, Preferenz S® series of amylases, Purastar® and Purastar® Ox Am, Optisize® HT Plus (all Du Pont). A suitable amylase is described in WO06/002643.

It may be particularly preferred for the compositions of the present invention to additionally comprise a cellulase enzyme. Suitable cellulases include those of bacterial or fungal origin. Chemically modified or protein engineered mutants are also suitable. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum*.

Commercially available cellulases include Celluzyme®, Carezyme®, and Carezyme® Premium, Celluclean® and Whitezyme® (Novozymes A/S), Revitalenz® series of enzymes (Du Pont), and Biotouch® series of enzymes (AB Enzymes). Suitable commercially available cellulases include Carezyme® Premium, Celluclean® Classic. Suitable cellulases are described in WO07/144857 and WO10/056652.

Chelant

The detergent composition herein typically comprises a chelant at a level of from 0.1% to 20%, preferably from 0.2% to 5%, more preferably from 0.2% to 3% by weight of total composition.

As commonly understood in the detergent field, chelation herein means the binding or complexation of a bi- or multidentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates or scale, or forming encrustations on soils turning them harder to be removed. The ligand forms a chelate complex with the substrate. The term is reserved for complexes in which the metal ion is bound to two or more atoms of the chelant. Suitable chelating agents can be selected from the group consisting of amino carboxylates, amino phosphonates, polycarboxylate chelating agents and mixtures thereof.

Preferred chelants for use herein are the amino acids based chelants and preferably glutamic-N,N-diacetic acid (GLDA), methylglycine-N,N-diacetic acid (MGDA), and derivatives, and/or phosphonate based chelants and preferably diethylenetriamine penta methylphosphonic acid or hydroxyethyldiphosphonic acid. GLDA (salts and derivatives thereof) is especially preferred according to the invention, with the tetrasodium salt thereof being especially preferred.

Other chelants include homopolymers and copolymers of polycarboxylic acids and their partially or completely neutralized salts, monomeric polycarboxylic acids and hydroxycarboxylic acids and their salts. Suitable polycarboxylic acids are acyclic, alicyclic, heterocyclic and aromatic carboxylic acids, in which case they contain at least two carboxyl groups which are in each case separated from one another by, preferably, no more than two carbon atoms. A suitable hydroxycarboxylic acid is, for example, citric acid. Another suitable polycarboxylic acid is the homopolymer of acrylic acid. Preferred are the polycarboxylates end capped with sulfonates.

Solvents

When the cleaning composition is in the form of a liquid detergent composition, particularly a laundry or liquid dishwashing detergent it may further comprise one or more organic solvents, which can be present in an amount ranging from about 1 wt % to about 80 wt %, preferably 5 wt % to about 70 wt %, more preferably from about 10 wt % to about 60 wt %, even more preferably from about 15 wt % to about 50 wt %, and most preferably from about 20 wt % to about 45 wt %, by total weight of the composition. Preferably the composition comprises cleaning solvents, especially when the composition is a dishwashing composition.

Cleaning Solvents

The liquid compositions of the present invention may comprise a grease cleaning solvent, or mixtures thereof as a highly preferred optional ingredient. Suitable solvent is selected from the group consisting of: ethers and diethers having from 4 to 14 carbon atoms, preferably from 6 to 12 carbon atoms, and more preferably from 8 to 10 carbon atoms; glycols or alkoxylated glycols; alkoxylated aromatic alcohols; aromatic alcohols; alkoxylated aliphatic alcohols; aliphatic alcohols; C8-C14 alkyl and cycloalkyl hydrocarbons and halohydrocarbons; C6-C16 glycol ethers; alkanolamines; terpenes and mixtures thereof. Typically, the liquid composition herein may comprise up to 30%, preferably from 1% to 25%, more preferably from 1% to 20% and most preferably from 2% to 10% by weight of the total composition of said solvent or mixture thereof.

Because phase separation is a constant challenge for liquid detergent compositions, especially when the salt content in such compositions is high, the solvent system of the present invention is particularly designed to minimize the risk of phase separation. Specifically, the solvent system of the present invention is composed mostly of diols, such as ethylene glycol, diethylene glycol, propylene glycol, dipropylene glycol, butylene glycol, pentanediols, and combinations thereof. The diols are present in the liquid detergent composition of the present invention in a total amount ranging from about 2 wt % to about 50 wt %. Preferably, the composition contains ethylene, diethylene glycol, and/or propylene glycol in a total amount ranging from about 5 wt % to about 40 wt %. More preferably, the composition contains propylene glycol in the amount ranging from about 15 wt % to about 35 wt %. Other organic solvents may also be present, which include, but are not limited to: methanol, ethanol, glycerin, sodium cumene sulfonate, potassium cumene sulfonate, ammonium cumene sulfonate, sodium toluene sulfonate, potassium toluene sulfonate, sodium xylene sulfonate, potassium xylene sulfonate, ammonium xylene sulfonate, or mixtures thereof. Other lower alcohols, such C1-C4 alkanolamines, e.g., monoethanolamine and/or triethanolamine, may also be used. In a particularly preferred embodiment of the present invention, the liquid detergent compositions of the present invention also contain from about 5 wt % to about 20 wt %, preferably from 6 wt % to 18 wt %, more preferably from 8 wt % to 16 wt % of glycerin in addition to the diol(s).

The liquid detergent composition of the present invention preferably contains water in combination with the above-mentioned organic solvent(s) as carrier(s). In some embodiments, water is present in the liquid detergent compositions of the present invention in the amount ranging from about 20 wt % to about 90 wt %, preferably from about 25 wt % to 80 wt %, and more preferably from about 30 wt % to about 70 wt %. In other embodiments, water is absent and the composition is anhydrous. Highly preferred compositions afforded by the present invention are clear, isotropic liquids. The liquid detergent composition as described herein above may also contain an external structurant, which may be present in an amount ranging from about 0.001% to about 1.0%, preferably from about 0.05% to about 0.5%, more preferably from about 0.1% to about 0.3% by total weight of the composition. Suitable external structurants include those described, for example, in US2007/169741 and US2005/0203213. Particularly preferred external structurants for the practice of the present invention are selected from hydrogenated castor oil, which is also referred to as trihydroxylstearin and is commercially available under the tradename Thixin®, and optionally modified natural fibres such as citrus fibres.

The balance of the cleaning composition of the present invention typically contains from about 5 wt % to about 70 wt %, or about 10 wt % to about 60 wt % adjunct ingredients.

Suitable adjunct ingredients for laundry detergent products include: builders, chelating agents, dye transfer inhibiting agents, dispersants, rheology modifiers, catalytic materials, bleach activators, hydrogen peroxide, sources of hydrogen peroxide, preformed peracids, polymeric dispersing agents, clay soil removal/anti-redeposition agents, brighteners, suds suppressors, dyes, photobleaches, structure elasticizing agents, fabric softeners, carriers, hydrotropes, processing aids, solvents, hueing agents, anti-microbial agents, free perfume oils, pungent agents, aversive agents, emetic agents, bittering agents and/or pigments. In addition to the disclosure below, suitable examples of such other adjunct ingredients and levels of use are found in U.S. Pat. Nos. 5,576,282, 6,306,812, and 6,326,348. The precise nature of these adjunct ingredients and the levels thereof in the liquid laundry detergent composition will depend on factors like the specific type of the composition and the nature of the cleaning operation for which it is to be used.

Suitable adjunct ingredients for dish detergent products include: builders, chelants, conditioning polymers, cleaning polymers, surface modifying polymers, soil flocculating polymers, structurants, emollients, humectants, skin rejuvenating actives, carboxylic acids, scrubbing particles, bleach and bleach activators, perfumes, malodor control agents, pigments, dyes, opacifiers, beads, pearlescent particles, microcapsules, organic and inorganic cations such as alkaline earth metals such as Ca/Mg-ions and diamines, antibacterial agents, preservatives and pH adjusters and buffering means.

When the composition comprises a solid free-flowing particulate detergent composition preferably comprises a fully formulated laundry detergent composition, not a portion thereof such as a spray-dried, extruded or agglomerate particle that only forms part of the laundry detergent composition. Typically, the solid composition comprises a plurality of chemically different particles, such as spray-dried base detergent particles and/or agglomerated base detergent particles and/or extruded base detergent particles, in combination with one or more, typically two or more, or five or more, or even ten or more particles selected from: surfactant particles, including surfactant agglomerates, surfactant extrudates, surfactant needles, surfactant noodles, surfactant flakes; phosphate particles; zeolite particles; silicate salt particles, especially sodium silicate particles; carbonate salt particles, especially sodium carbonate particles; polymer particles such as carboxylate polymer particles, cellulosic polymer particles, starch particles, polyester particles, polyamine particles, terephthalate polymer particles, polyethylene glycol particles; aesthetic particles such as coloured noodles, needles, lamellae particles and ring particles; enzyme particles such as protease granulates, amylase granulates, lipase granulates, cellulase granulates, mannanase granulates, pectate lyase granulates, xyloglucanase granulates, bleaching enzyme granulates and co-granulates of any of these enzymes, preferably these enzyme granulates comprise sodium sulphate; bleach particles, such as percarbonate particles, especially coated percarbonate particles, such as percarbonate coated with carbonate salt, sulphate salt, silicate salt, borosilicate salt, or any combination thereof, perborate particles, bleach activator particles such as tetra acetyl ethylene diamine particles and/or alkyl oxybenzene sulphonate particles, bleach catalyst particles such as transition metal catalyst particles, and/or isoquinolinium bleach catalyst particles, pre-formed peracid particles, especially coated pre-formed peracid particles; filler particles such as sulphate salt particles and chloride particles; clay particles such as montmorillonite particles and particles of clay and silicone; flocculant particles such as polyethylene oxide particles; wax particles such as wax agglomerates; silicone particles, brightener particles; dye transfer inhibition particles; dye fixative particles; perfume particles such as perfume microcapsules and starch encapsulated perfume accord particles, or pro-perfume particles such as Schiff base reaction product particles; hueing dye particles; chelant particles such as chelant agglomerates; and any combination thereof.

Polymers

Carboxylate Polymer:

The composition may comprise a carboxylate polymer, such as a maleate/acrylate random copolymer or polyacrylate homopolymer. Suitable carboxylate polymers include: polyacrylate homopolymers having a molecular weight of from 4,000 Da to 9,000 Da; maleate/acrylate random copolymers having a molecular weight of from 50,000 Da to 100,000 Da, or from 60,000 Da to 80,000 Da.

Another suitable carboxylate polymer is a co-polymer that comprises: (i) from 50 to less than 98 wt % structural units derived from one or more monomers comprising carboxyl groups; (ii) from 1 to less than 49 wt % structural units derived from one or more monomers comprising sulfonate moieties; and (iii) from 1 to 49 wt % structural units derived from one or more types of monomers selected from ether bond-containing monomers represented by formulas (I) and (II):

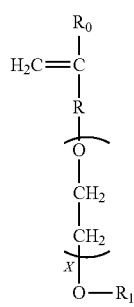

formula (I)

wherein in formula (I), $R_0$ represents a hydrogen atom or $CH_3$ group, R represents a $CH_2$ group, $CH_2CH_2$ group or single bond, X represents a number 0-5 provided X represents a number 1-5 when R is a single bond, and $R_1$ is a hydrogen atom or $C_1$ to $C_{20}$ organic group;

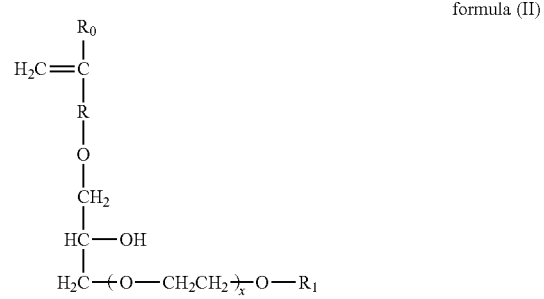

formula (II)

wherein in formula (II), $R_0$ represents a hydrogen atom or $CH_3$ group, R represents a $CH_2$ group, $CH_2CH_2$ group or single bond, X represents a number 0-5, and $R_1$ is a hydrogen atom or $C_1$ to C20 organic group.

It may be preferred that the polymer has a weight average molecular weight of at least 50 kDa, or even at least 70 kDa.

Soil Release Polymer:

The composition may comprise a soil release polymer. A suitable soil release polymer has a structure as defined by one of the following structures (I), (II) or (III):

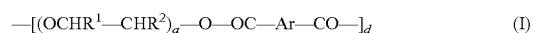  (I)

  (II)

  (III)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{15}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are sold by Clariant under the TexCare® series of polymers, e.g. TexCare® SRN240 and TexCare® SRA300. Other suitable soil release polymers are sold by Solvay under the Repel-o-Tex® series of polymers, e.g. Repel-o-Tex® SF2 and Repel-o-Tex® Crystal.

Anti-Redeposition Polymer:

Suitable anti-redeposition polymers include polyethylene glycol polymers and/or polyethyleneimine polymers.

Suitable polyethylene glycol polymers include random graft co-polymers comprising: (i) hydrophilic backbone comprising polyethylene glycol; and (ii) hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Suitable polyethylene glycol polymers are described in WO08/007320.

Cellulosic Polymer:

Suitable cellulosic polymers are selected from alkyl cellulose, alkyl alkoxyalkyl cellulose, carboxyalkyl cellulose, alkyl carboxyalkyl cellulose, sulphoalkyl cellulose, more preferably selected from carboxymethyl cellulose, methyl cellulose, methyl hydroxyethyl cellulose, methyl carboxymethyl cellulose, and mixtures thereof.

Suitable carboxymethyl celluloses have a degree of carboxymethyl substitution from 0.5 to 0.9 and a molecular weight from 100,000 Da to 300,000 Da.

Suitable carboxymethyl celluloses have a degree of substitution greater than 0.65 and a degree of blockiness greater than 0.45, e.g. as described in WO09/154933.

Care Polymers:

Suitable care polymers include cellulosic polymers that are cationically modified or hydrophobically modified. Such modified cellulosic polymers can provide anti-abrasion benefits and dye lock benefits to fabric during the laundering cycle. Suitable cellulosic polymers include cationically modified hydroxyethyl cellulose.

Other suitable care polymers include dye lock polymers, for example the condensation oligomer produced by the condensation of imidazole and epichlorhydrin, preferably in ratio of 1:4:1. A suitable commercially available dye lock polymer is Polyquart® FDI (Cognis).

Other suitable care polymers include amino-silicone, which can provide fabric feel benefits and fabric shape retention benefits.

Bleach:

Suitable bleach includes sources of hydrogen peroxide, bleach activators, bleach catalysts, pre-formed peracids and any combination thereof. A particularly suitable bleach includes a combination of a source of hydrogen peroxide with a bleach activator and/or a bleach catalyst.

Source of Hydrogen Peroxide:

Suitable sources of hydrogen peroxide include sodium perborate and/or sodium percarbonate.

Bleach Activator:

Suitable bleach activators include tetra acetyl ethylene diamine and/or alkyl oxybenzene sulphonate.

Bleach Catalyst:

The composition may comprise a bleach catalyst. Suitable bleach catalysts include oxaziridinium bleach catalysts, transition metal bleach catalysts, especially manganese and iron bleach catalysts. A suitable bleach catalyst has a structure corresponding to general formula below:

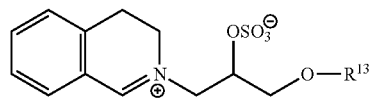

wherein $R^{13}$ is selected from the group consisting of 2-ethylhexyl, 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl.

Pre-Formed Peracid:

Suitable pre-form peracids include phthalimido-peroxy-caproic acid.

Brightener:

Suitable fluorescent brighteners include: di-styryl biphenyl compounds, e.g. Tinopal® CBS-X, di-amino stilbene di-sulfonic acid compounds, e.g. Tinopal® DMS pure Xtra and Blankophor® HRH, and Pyrazoline compounds, e.g. Blankophor® SN, and coumarin compounds, e.g. Tinopal® SWN.

Preferred brighteners are: sodium 2 (4-styryl-3-sulfophenyl)-2H-napthol[1,2-d]triazole, disodium 4,4'-bis{[(4-anilino-6-(N methyl-N-2 hydroxyethyl)amino 1,3,5-triazin-2-yl)]; amino}stilbene-2-2' disulfonate, disodium 4,4'-bis{[(4-anilino-6-morpholino-1,3,5-triazin-2-yl)]amino} stilbene-2-2' disulfonate, and disodium 4,4'-bis(2-sulfostyryl)biphenyl. A suitable fluorescent brightener is C.I. Fluorescent Brightener 260, which may be used in its beta or alpha crystalline forms, or a mixture of these forms.

Hueing Agent:

Suitable hueing agents include small molecule dyes, typically falling into the Colour Index (C.I.) classifications of Acid, Direct, Basic, Reactive (including hydrolysed forms thereof) or Solvent or Disperse dyes, for example classified as Blue, Violet, Red, Green or Black, and provide the desired shade either alone or in combination. Preferred such hueing agents include Acid Violet 50, Direct Violet 9, 66 and 99, Solvent Violet 13 and any combination thereof.

Many hueing agents are known and described in the art which may be suitable for the present invention, such as hueing agents described in WO2014/089386.

Suitable hueing agents include phthalocyanine and azo dye conjugates, such as described in WO2009/069077.

Suitable hueing agents may be alkoxylated. Such alkoxylated compounds may be produced by organic synthesis that may produce a mixture of molecules having different degrees of alkoxylation. Such mixtures may be used directly to provide the hueing agent, or may undergo a purification step to increase the proportion of the target molecule. Suitable hueing agents include alkoxylated bis-azo dyes, such as described in WO2012/054835, and/or alkoxylated thiophene azo dyes, such as described in WO2008/087497 and WO2012/166768.

The hueing agent may be incorporated into the detergent composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route. Suitable hueing agents can be incorporated into hueing dye particles, such as described in WO 2009/069077.

Dye Transfer Inhibitors:

Suitable dye transfer inhibitors include polyamine N-oxide polymers, copolymers of N-vinylpyrrolidone and N-vinylimidazole, polyvinylpyrrolidone, polyvinyloxazolidone, polyvinylimidazole and mixtures thereof. Preferred are poly(vinyl pyrrolidone), poly(vinylpyridine betaine), poly(vinylpyridine N-oxide), poly(vinyl pyrrolidone-vinyl imidazole) and mixtures thereof. Suitable commercially available dye transfer inhibitors include PVP-K15 and K30 (Ashland), Sokalan® HP165, HP50, HP53, HP59, HP56K, HP56, HP66 (BASF), Chromabond® S-400, 5403E and S-100 (Ashland).

Perfume:

Suitable perfumes comprise perfume materials selected from the group: (a) perfume materials having a C log P of less than 3.0 and a boiling point of less than 250° C. (quadrant 1 perfume materials); (b) perfume materials having a C log P of less than 3.0 and a boiling point of 250° C. or greater (quadrant 2 perfume materials); (c) perfume materials having a C log P of 3.0 or greater and a boiling point of less than 250° C. (quadrant 3 perfume materials); (d) perfume materials having a C log P of 3.0 or greater and a boiling point of 250° C. or greater (quadrant 4 perfume materials); and (e) mixtures thereof.

It may be preferred for the perfume to be in the form of a perfume delivery technology. Such delivery technologies further stabilize and enhance the deposition and release of perfume materials from the laundered fabric. Such perfume delivery technologies can also be used to further increase the longevity of perfume release from the laundered fabric. Suitable perfume delivery technologies include: perfume microcapsules, pro-perfumes, polymer assisted deliveries, molecule assisted deliveries, fiber assisted deliveries, amine assisted deliveries, cyclodextrin, starch encapsulated accord, zeolite and other inorganic carriers, and any mixture thereof. A suitable perfume microcapsule is described in WO2009/101593.

A preferred detergent composition is preferably a manual dishwashing detergent, preferably in liquid form. It typically contains from 30% to 95%, preferably from 40% to 90%, more preferably from 50% to 85% by weight of a liquid carrier in which the other essential and optional components are dissolved, dispersed or suspended. One preferred component of the liquid carrier is water.

Preferably the pH of the detergent is adjusted to between 3 and 14, more preferably between 4 and 13, more preferably between 6 and 12 and most preferably between 8 and 10. The pH of the detergent can be adjusted using pH modifying ingredients known in the art.

EXAMPLES

Hereinafter, the present invention is described in more detail based on examples. All percentages are by weight unless otherwise specified. Articles soiled with oily soils are washed using the compositions described and increased suds longevity is provided compared to the same compositions not comprising the fatty acid-transforming enzyme.

Example 1

The foam generating potential of an enzyme-free reference composition was compared to the foam generating potential of a test composition comprising the reference formulation with the enzyme following the testing protocol described below. Olive oil has been added as a source of fatty acid.

Testing Protocol:

A wash solution was prepared by diluting below reference formulation in water (15 dH water hardness, 20° C.) at a product concentration of 0.12%. 11 g of this wash solution was added to a 40 ml glass vial (diameter of 28 mm and height of 95 mm). No enzymes were added for the reference leg. 90 ppm of oleic hydratase fatty acid-transforming enzyme according to SEQ ID NO: 1 was added on top of the reference leg for test leg A. 90 ppm of oleic hydratase fatty acid-transforming enzyme according to SEQ ID NO: 2 was added on top of the reference leg for test leg B. 90 ppm of Linoleate Lipoxygenase fatty acid-transforming enzyme (type: EC 1.13.11.77-oleate 10S-lipoxygenase, which can be produced as described in "Antonie van Leeuwenhoek (2005) 87:245-251") was added on top of the reference leg for test leg C. Test legs A, B and C are examples according to the invention, while the reference leg is a comparative example outside the scope of the invention.

0.22 g of Olive Oil (Bertoli:Olio Extra Vergine Di Oliva—Originale) was further added to each vial. A magnetic stirrer (size: 8 mm length, 3 mm diameter) was added to each vial, and each solution was stirred on a magnetic stirring plate for 2 minutes at a vortex reaching half of the liquid height. The resulting homogenized samples were consequently hand-shaken together in an up and down motion over a distance of about 20 cm up and 20 cm down for 20 seconds at frequency of 120 shakes per minute at a 45 degree shake amplitude. One shake comprises one up and one down motion. The 3 test vials were then put for 1 hour in a warm water bath at 35° C. on a magnetic stirring plate stirred at 500 rpm. The foam height (cm) of the aged samples was consequently measured after another round of hand shaking for 20 seconds, as described above.

Reference Formulation:

| Ingredient | 100% active level |
| --- | --- |
| C 12-13AE0.6S anionic surfactant | 10.5% |
| C 12-14 alkyldimethyl amine oxide | 3.5% |
| NaCl | 0.4 |
| Ethanol | 1.1 |
| Polypropyleneglycol (MW 2000) | 0.6 |
| Water and minors (perfume, dye, preservative) | Balance to 100% |

Test Results:

It can be seen from the foam height data summarized below that the compositions comprising one of the fatty acid-transforming enzymes build up more foam compared to an enzyme-free comparative example.

| | ppm pure enzyme in vial | Foam height (cm) |
| --- | --- | --- |
| Reference formulation | — | 0 |
| Test leg A Oleic hydratase (SEQ ID NO: 1) | 90 | 0.4 |
| Test leg B Oleic hydratase - (SEQ ID NO: 2) | 90 | 0.5 |
| Test leg C Linoleate Lipoxygenase | 90 | 0.4 |

Example 2

Exemplary Manual Dish-Washing Detergent Composition

| | Level (as 100% active) | | |
| --- | --- | --- | --- |
| | 1A | 1B | 1C |
| Sodium alkyl ethoxy sulfate (C1213EO0.6S) | 22.91% | 22.91% | 22.91% |
| n-C12-14 Di Methyl Amine Oxide | 7.64% | 7.64% | 7.64% |
| Lutensol XP80 (non-ionic surfactant supplied by BASF) | 0.45% | 0.45% | 0.45% |
| Sodium Chloride | 1.2% | 1.2% | 1.2% |
| Poly Propylene Glycol | 1% | 1% | 1% |
| Ethanol | 2% | 2% | 2% |
| Sodium Hydroxide | 0.24% | 0.24% | 0.24% |

-continued

| | Level (as 100% active) | | |
|---|---|---|---|
| | 1A | 1B | 1C |
| Oleate hydratase from table 1 | 0.1% | 0.1% | 0.1% |
| Oleate lipoxygenase | 0.05% | 0.04% | 0.1% |
| Fatty acid decarboxylase | 0.08% | 0.1% | 0.01% |
| Minors (perfume, preservative, dye) + water | To 100% | To 100% | To 100% |
| pH (@ 10% solution) | 9 | 9 | 9 |

Example 3

Exemplary Liquid Laundry Detergent Compositions

The following liquid laundry detergent compositions are prepared by traditional means known to those of ordinary skill in the art by mixing the following ingredients.

| Ingredients (wt %) | 2A | 2B | 2C |
|---|---|---|---|
| AES[1] | 17 | 2 | 11 |
| LAS[2] | 2.8 | 15 | 10 |
| AE[3] | 2.3 | 2.37 | 3.44 |
| Citric Acid | 5 | 1.98 | — |
| Boric Acid | — | 1 | 3 |
| Amine Oxide | 1.2 | — | 0.5 |
| Trimethyl Lauryl Ammonium Chloride | — | 1.5 | — |
| PEI Polymer | 0.1~3.5 | 1 | 2 |
| Fatty Acids | 1.2 | 1.2 | 1.2 |
| Protease (54.5 mg/g)[4] | 7.62 | 7.98 | 2.08 |
| Amylase (29.26 mg/g)[5] | 2.54 | 2.67 | 0.69 |
| Xyloglucanase[6] | — | — | 0.15 |
| Oleate hydratase | — | 0.2 | 0.05 |
| Oleate lipoxgenase | 0.2 | — | — |
| Borax | 4.72 | 4.94 | — |
| Calcium Formate | 0.15 | 0.16 | 0.16 |
| Amphiphilic polymer[7] | — | 1.5 | 4.36 |
| Hexamethylene diamine, ethoxylated, quaternized, sulfated[8] | — | — | 1.68 |
| DTPA[9] (50% active) | 0.28 | 0.3 | 0.64 |
| Tiron ® | 0.84 | 0.89 | — |
| Optical Brightener[10] | 0.34 | 0.37 | 0.36 |
| Ethanol | 0.97 | 4.1 | 2.99 |
| Propylene Glycol | 4.9 | 5.16 | 8.49 |
| Diethylene Glycol | — | — | 4.11 |
| Monoethanolamine (MEA) | 1.12 | 1.17 | 0.23 |
| Caustic Soda (NaOH) | 3.5 | 3.74 | 2.1 |
| Na Formate | 0.61 | 0.64 | 0.23 |
| Na Cumene Sulfonate | — | — | 1 |
| Suds Suppressor | — | — | 0.18 |
| Dye | 0.01 | — | 0.02 |
| Perfume | 0.85 | — | 1 |
| Preservative[11] | 0.05 | 0.5 | — |
| Hydrogenated castor oil | — | — | 0.27 |
| Water | Q.S. | Q.S. | Q.S. |

Example 4

Exemplary Liquid Detergent Compositions for Use in Unit Dose (UD) Products

The following liquid detergent compositions are prepared and encapsulated in a multi-compartment pouch formed by a polyvinyl alcohol-film.

TABLE 6

| | A | B |
|---|---|---|
| Usage (g) | 25.36 | 24.34 |
| Usage (ml) | 23.7 | 22.43 |
| Wash Volume (L) | 64 | 64 |
| Anionic/Nonionic ratio | 1.73 | 9.9 |
| Ingredients (wt %) | | |
| Linear $C_9$-$C_{15}$ Alkylbenzene sulfonic acid | 18.25 | 22.46 |
| HC24/25 AE2/3S 90/10 blend | 8.73 | 15.29 |
| $C_{12-14}$ alkyl 9-ethoxylate | 15.56 | 3.82 |
| Citric Acid | 0.65 | 1.55 |
| Fatty acid | 6.03 | 6.27 |
| Chelants | 1.16 | 0.62 |
| PEI Polymers | 1~6 | 3 |
| S Copolymers | 1~6 | 3 |
| Enzymes | 0.11 | 0.12 |
| Oleate hydratase from table 1 or oleate lipoxygenase | 0.003 | 0.01 |
| Optical Brightener[15] | 0.18 | 0.19 |
| Structurant | 0.1 | 0.1 |
| Solvent system* | 20.31 | 17.96 |
| Water | 10.31 | 11.66 |
| Perfume | 1.63 | 1.7 |
| Aesthetics | 1.48 | 1.13 |
| Mono-ethanolamine or NaOH (or mixture thereof) | 6.69 | 9.75 |
| Other laundry adjuncts/minors | Q.S. | Q.S. |

*May include, but not limited to propanediol, glycerol, ethanol, dipropyleneglycol, polyetheyleneglycol, polypropyleneglycol.

Example 5

Granular laundry detergent compositions for hand washing or washing machines, typically top-loading washing machines.

| Ingredient | 4A | 4B | 4C | 4D | 4E | 4F |
|---|---|---|---|---|---|---|
| | % weight | | | | | |
| LAS[2] | 11.33 | 10.81 | 7.04 | 4.20 | 3.92 | 2.29 |
| $C_{12-14}$Dimethylhydroxyethyl ammonium chloride | 0.70 | 0.20 | 1.00 | 0.60 | — | — |
| AES[1] | 0.51 | 0.49 | 0.32 | — | 0.08 | 0.10 |
| AE[3] | 8.36 | 11.50 | 12.54 | 11.20 | 16.00 | 21.51 |
| Sodium Tripolyphosphate | 5.0 | — | 4.0 | 9.0 | 2.0 | — |
| Zeolite A | — | 1.0 | — | 1.0 | 4.0 | 1.0 |
| Sodium silicate 1.6R | 7.0 | 5.0 | 2.0 | 3.0 | 3.0 | 5.0 |
| Sodium carbonate | 20.0 | 17.0 | 23.0 | 14.0 | 14.0 | 16.0 |

-continued

| Ingredient | 4A | 4B | 4C | 4D | 4E | 4F |
|---|---|---|---|---|---|---|
| | | | % weight | | | |
| Polyacrylate MW 4500 | 1.0 | 0.6 | 1.0 | 1.0 | 1.5 | 1.0 |
| Polymer grafted with vinyl acetate side chains[7] | 0.1 | 0.2 | — | — | 0.1 | — |
| Carboxymethyl cellulose | 1.0 | 0.3 | 1.0 | 1.0 | 1.0 | 1.0 |
| Acid Violet 50 | 0.05 | — | 0.02 | — | 0.04 | — |
| Violet DD thiophene azo dye (Milliken) | — | 0.03 | — | 0.03 | — | 0.03 |
| Protease[4] | 0.10 | 0.10 | 0.10 | 0.10 | — | 0.10 |
| Amylase[5] | 0.03 | — | 0.03 | 0.03 | 0.03 | 0.03 |
| Lipase (Lipex from Novozymes) | 0.03 | 0.07 | 0.30 | 0.10 | 0.07 | 0.40 |
| Cellulase (Celluclean from Novozymes) | 0.002 | — | 0.05 | — | 0.02 | — |
| Oleate Hydratase from Table 1 | 0.001 | 0.001 | 0.01 | 0.05 | 0.002 | 0.02 |
| Dispersin B (glycosidase hydrolase, reported as 1000 mg active/g) | 0.001 | 0.001 | 0.05 | — | 0.001 | — |
| Optical Brightener[15] | 0.300 | 0.011 | 0.370 | 0.850 | 0.10 | 0.710 |
| Chelant[13] | 0.60 | 0.80 | 0.60 | 0.25 | 0.60 | 0.60 |
| DTI[12] | 0.62 | 0.35 | 0.15 | 0.30 | 0.20 | 0.40 |
| Sodium Percarbonate | — | 5.2 | 0.1 | — | — | — |
| Sodium Perborate | 4.4 | — | 3.85 | 2.09 | 0.78 | 3.63 |
| Nonanoyloxy benzensulphonate | 1.9 | 0.0 | 1.66 | 0.0 | 0.33 | 0.75 |
| Tetraacetylethylenediamine | 0.58 | 1.2 | 0.51 | 0.0 | 0.015 | 0.28 |
| Photobleach | 0.0030 | 0.0 | 0.0012 | 0.0030 | 0.0021 | — |
| S-ACMC[14] | 0.1 | 0.0 | 0.0 | 0.0 | 0.06 | 0.0 |
| Sulfate/Moisture | | | Balance | | | |

[1] AES can be $AE_{1.5}S$, $AE_2S$, and/or $AE_3S$, in the amount ranging from 0-20%.
[2] LAS can be provided in the amount ranging from 0-20%.
[3] AE is a C12-14 alcohol ethoxylate, with an average degree of ethoxylation of 7-9, supplied by Huntsman, Salt Lake City, Utah, USA. It can be provided in the amount ranging from 0-10%.
[4] Proteases may be supplied by Genencor International, Palo Alto, California, USA (e.g., Purafect Prime ®, Excellase ®) or by Novozymes, Bagsvaerd, Denmark (e.g. Liquanase ®, Coronase ®).
[5] Available from Novozymes, Bagsvaerd, Denmark (e.g., Natalase ®, Mannaway ®).
[6] Available from Novozymes (e.g., Whitezyme ®).
[7] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units, available from BASF as Sokalan PG101 ®.
[8] A compound having the following general structure: $bis((C_2H_5O)(C_2H_4O)_n)(CH_3)\text{—}N^+\text{—}C_xH_{2x}\text{—}N^+\text{—}(CH_3)\text{-}bis((C_2H_5O)(C_2H_4O)_n)$, wherein n = from 20 to 30, and x = from 3 to 8, or sulphated or sulphonated variants thereof, available from BASF as Lutenzit Z 96 ®
[9] DTPA is diethylenetriaminepentaacetic acid supplied by Dow Chemical, Midland, Michigan, USA.
[10] Suitable Fluorescent Whitening Agents are for example, Tinopal ® AMS, Tinopal ® CBS-X, Sulphonated zinc phthalocyanine Ciba Specialty Chemicals, Basel, Switzerland. It can be provided in the amount ranging from 0-5%.
[11] Suitable preservatives include methylisothiazolinone (MIT) or benzisothiazolinone (BIT), which can be provided in the amount ranging from 0-1%.
[12] DTI is poly(4-vinylpyridine-1-oxide) (such as Chromabond S-403E ®) and/or poly(1-vinylpyrrolidone-co-1-vinylimidazole) (such as Sokalan HP56 ®).
[13] Chelant is diethylene triamine pentaacetic acid, 1-hydroxyethane 1,1-diphosphonic acid and/or sodium salt of ethylenediamine-N,N'-disuccinic acid, (S,S) isomer (EDDS)
[14] S-ACMC is Rective Blue 19 Azo-CM-Cellulose provided by Megazyme
[15] Optical brightener is disodium 4,4'-bis{[4-anilino-6-morpholino-s-triazin-2-yl]-amino}-2,2'-stilbenedisulfonate, disodium 4,4'-bis-(2-sulfostyryl)biphenyl (sodium salt) and/or Optiblanc SPL10 ® from 3V Sigma All percentages and ratios given for enzymes are based on active protein. All percentages and ratios herein are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manually washing dishware, comprising the step of: delivering a cleaning composition comprising a fatty acid-transforming enzyme to a volume of water to form a wash liquor and immersing the dishware in the liquor, in the presence of oily or fatty soils, wherein the fatty acid transforming enzyme is an oleate hydratase having E.C. classification 4.2.1.53, wherein the fatty acid transforming enzyme increases the duration of suds during washing of the dishware.

2. The method according to claim 1 wherein the composition is applied onto a cleaning implement; the cleaning implement is used to apply the composition to the dishware and water is added to the dishware and composition to form the wash liquor.

3. The method according to claim 1 wherein the composition comprises from about 5 to about 80 wt % of the composition of a surfactant system.

4. The method according to claim 1 wherein the fatty acid-transforming enzyme comprises an oleic-acid transforming enzyme having at least about 60% identity to the wild type oleate hydratase of *Elizabethkingia meningoseptica* (SEQ ID NO. 1).

5. The method according to claim 1 wherein the fatty acid-transforming enzyme is present in the composition in an amount from about 0.0001 wt % to about 1 wt % based on active protein.

6. The method according to claim 5 wherein the fatty acid-transforming enzyme is present in the composition in an amount from about 0.001 to about 0.2 wt % based on active protein.

7. The method according to claim 1 wherein the fatty acid-transforming enzyme is present in the wash liquor at a concentration of about 0.005 ppm to about 3.0 ppm.

8. The method according to claim 1 wherein the fatty acid-transforming enzyme is present in the aqueous wash liquor used at a concentration of about 0.02 ppm to about 0.5 ppm based on active protein.

9. The method according to claim 1 wherein the detergent composition comprises a surfactant system, said surfactant system comprising an amphoteric and/or a zwitterionic surfactant.

10. The method according to claim 9 wherein said surfactant system comprising an amphoteric and/or a zwitterionic surfactant further comprises an anionic surfactant.

11. The method according to claim 10 wherein the anionic surfactant and the amphoteric and/or the zwitterionic surfactant are in a weight ratio of less than about 9:1.

12. The method according to claim 11 wherein the anionic surfactant and the amphoteric and/or and/or zwitterionic surfactant are in a weight ratio from about 5:1 to about 1:1.

13. The method according to claim 11 wherein the anionic surfactant and the amphoteric and/or zwitterionic surfactant are in a weight ratio from about 4:1 to about 2:1.

14. The method according to claim 9 wherein the amphoteric surfactant comprises an amine oxide surfactant and the zwitterionic surfactant comprises a betaine surfactant.

15. The method according to claim 1 additionally comprising an enzyme stabilizer selected from the group consisting of chemical and physical stabilisers, wherein the physical stabiliser comprises encapsulated enzyme.

16. The method according to claim 1 wherein the detergent composition comprises chelant.

17. The method according to claim 1 wherein the detergent composition comprises chelant selected from amino carboxylate chelant, amino phosphonate chelant, or mixtures thereof.

18. The method of claim 14, wherein the surfactant system comprises an anionic surfactant selected from the group consisting of alkyl sulfate, alkyl alkoxy sulfate, and mixtures thereof, in combination with an amine oxide surfactant in a weight ratio of less than 9:1.

19. The method of claim 18, wherein the surfactant system comprises alkyl ethoxy sulfate in combination with an amine oxide surfactant in a weight ratio from about 5:1 to 1:2.

* * * * *

SEQUENCE LISTING

<160> NUMBER OF SEQ ID NOS: 12

<210> SEQ ID NO 1
<211> LENGTH: 646
<212> TYPE: PRT
<213> ORGANISM: Elizabethkingia meningoseptica

<400> SEQUENCE: 1

```
Met Asn Pro Ile Thr Ser Lys Phe Asp Lys Val Leu Asn Ala Ser Ser
1               5                   10                  15

Glu Tyr Gly His Val Asn His Glu Pro Asp Ser Ser Lys Glu Gln Gln
            20                  25                  30

Arg Asn Thr Pro Gln Lys Ser Met Pro Phe Ser Asp Gln Ile Gly Asn
        35                  40                  45

Tyr Gln Arg Asn Lys Gly Ile Pro Val Gln Ser Tyr Asp Asn Ser Lys
    50                  55                  60

Ile Tyr Ile Ile Gly Ser Gly Ile Ala Gly Met Ser Ala Ala Tyr Tyr
65                  70                  75                  80

Phe Ile Arg Asp Gly His Val Pro Ala Lys Asn Ile Thr Phe Leu Glu
                85                  90                  95

Gln Leu His Ile Asp Gly Gly Ser Leu Asp Gly Ala Gly Asn Pro Thr
            100                 105                 110

Asp Gly Tyr Ile Ile Arg Gly Gly Arg Glu Met Asp Met Thr Tyr Glu
        115                 120                 125

Asn Leu Trp Asp Met Phe Gln Asp Ile Pro Ala Leu Glu Met Pro Ala
    130                 135                 140

Pro Tyr Ser Val Leu Asp Glu Tyr Arg Leu Ile Asn Asp Asn Asp Ser
145                 150                 155                 160

Asn Tyr Ser Lys Ala Arg Leu Ile Asn Asn Lys Gly Glu Ile Lys Asp
                165                 170                 175

Phe Ser Lys Phe Gly Leu Asn Lys Met Asp Gln Leu Ala Ile Ile Arg
            180                 185                 190

Leu Leu Leu Lys Asn Lys Glu Glu Leu Asp Asp Leu Thr Ile Glu Asp
        195                 200                 205

Tyr Phe Ser Glu Ser Phe Leu Lys Ser Asn Phe Trp Thr Phe Trp Arg
    210                 215                 220

Thr Met Phe Ala Phe Glu Asn Trp His Ser Leu Leu Glu Leu Lys Leu
225                 230                 235                 240

Tyr Met His Arg Phe Leu His Ala Ile Asp Gly Leu Asn Asp Leu Ser
                245                 250                 255

Ser Leu Val Phe Pro Lys Tyr Asn Gln Tyr Asp Thr Phe Val Thr Pro
            260                 265                 270

Leu Arg Lys Phe Leu Gln Glu Lys Gly Val Asn Ile His Leu Asn Thr
        275                 280                 285

Leu Val Lys Asp Leu Asp Ile His Ile Asn Thr Glu Gly Lys Val Val
    290                 295                 300

Glu Gly Ile Ile Thr Glu Gln Asp Gly Lys Glu Val Lys Ile Pro Val
305                 310                 315                 320

Gly Lys Asn Asp Tyr Val Ile Val Thr Thr Gly Ser Met Thr Glu Asp
                325                 330                 335

Thr Phe Tyr Gly Asn Asn Lys Thr Ala Pro Ile Ile Gly Ile Asp Asn
            340                 345                 350

Ser Thr Ser Gly Gln Ser Ala Gly Trp Lys Leu Trp Lys Asn Leu Ala
        355                 360                 365
```

```
Ala Lys Ser Glu Ile Phe Gly Lys Pro Glu Lys Phe Cys Ser Asn Ile
    370                 375                 380

Glu Lys Ser Ala Trp Glu Ser Ala Thr Leu Thr Cys Lys Ser Ser Ala
385                 390                 395                 400

Leu Ile Asp Lys Leu Lys Glu Tyr Ser Val Asn Asp Pro Tyr Ser Gly
                405                 410                 415

Lys Thr Val Thr Gly Gly Ile Ile Thr Ile Thr Asp Ser Asn Trp Leu
            420                 425                 430

Met Ser Phe Thr Cys Asn Arg Gln Pro His Phe Pro Glu Gln Pro Asp
        435                 440                 445

Asp Val Leu Val Leu Trp Val Tyr Ala Leu Phe Met Asp Lys Glu Gly
    450                 455                 460

Asn Tyr Ile Lys Lys Thr Met Pro Glu Cys Thr Gly Asp Glu Ile Leu
465                 470                 475                 480

Ala Glu Leu Cys Tyr His Leu Gly Ile Glu Asp Gln Leu Glu Asn Val
                485                 490                 495

Gln Lys Asn Thr Ile Val Arg Thr Ala Phe Met Pro Tyr Ile Thr Ser
            500                 505                 510

Met Phe Met Pro Arg Ala Lys Gly Asp Arg Pro Arg Val Val Pro Glu
        515                 520                 525

Gly Cys Lys Asn Leu Gly Leu Val Gly Gln Phe Val Glu Thr Asn Asn
    530                 535                 540

Asp Val Val Phe Thr Met Glu Ser Ser Val Arg Thr Ala Arg Ile Ala
545                 550                 555                 560

Val Tyr Lys Leu Leu Asn Leu Asn Lys Gln Val Pro Asp Ile Asn Pro
                565                 570                 575

Leu Gln Tyr Asp Ile Arg His Leu Leu Lys Ala Ala Lys Thr Leu Asn
            580                 585                 590

Asp Asp Lys Pro Phe Val Gly Glu Gly Leu Leu Arg Lys Val Leu Lys
        595                 600                 605

Gly Thr Tyr Phe Glu His Val Leu Pro Ala Gly Ala Ala Glu Glu Glu
    610                 615                 620

Glu His Glu Ser Phe Ile Ala Glu His Val Asn Lys Phe Arg Glu Trp
625                 630                 635                 640

Val Lys Gly Ile Arg Gly
                645

<210> SEQ ID NO 2
<211> LENGTH: 590
<212> TYPE: PRT
<213> ORGANISM: Lysinibacillus fusiformis

<400> SEQUENCE: 2

Met Tyr Tyr Ser Asn Gly Asn Tyr Glu Ala Phe Ala Arg Pro Lys Lys
1               5                   10                  15

Pro Glu Gly Val Asp Glu Lys Ser Ala Tyr Leu Ile Gly Ser Gly Leu
            20                  25                  30

Ala Ser Leu Ser Ala Ala Cys Phe Leu Ile Arg Asp Gly Gln Met Lys
        35                  40                  45

Gly Glu Asn Ile His Ile Leu Glu Glu Leu Asp Ile Ser Gly Gly Ser
    50                  55                  60

Leu Asp Gly Ile Leu Asn Pro Thr Arg Gly Phe Ile Ile Arg Gly Gly
65                  70                  75                  80

Arg Glu Met Glu Asp His Phe Glu Cys Leu Trp Asp Leu Phe Arg Ser
                85                  90                  95
```

-continued

```
Ile Pro Ser Leu Glu Val Glu Asn Ala Ser Val Leu Asp Glu Phe Tyr
            100                 105                 110

Trp Leu Asn Lys Glu Asp Pro Asn Tyr Ser Lys Cys Arg Leu Met Lys
            115                 120                 125

Asp Arg Gly Gln Arg Leu Glu Asp Asp Gly Lys Phe Thr Leu Ser Asp
        130                 135                 140

Lys Ser Ser Glu Glu Met Ile Lys Leu Phe Phe Thr Pro Glu Lys
145                 150                 155                 160

Leu Glu Asp Lys Lys Ile Thr Asp Val Phe Ser Asp Glu Phe Phe Glu
                165                 170                 175

Ser Asn Phe Trp Leu Tyr Trp Ser Thr Met Phe Ala Phe Glu Lys Trp
            180                 185                 190

His Ser Ala Met Glu Met Arg Arg Tyr Ile Met Arg Phe Ile His His
        195                 200                 205

Ile Gly Gly Leu Pro Asp Leu Ser Ala Leu Lys Phe Thr Lys Tyr Asn
    210                 215                 220

Gln Tyr Glu Ser Leu Val Leu Pro Met Ile Lys Tyr Leu Glu Ser His
225                 230                 235                 240

Asp Val Asp Phe Gln Tyr Asn Thr Val Glu Asn Val Leu Val Asp
                245                 250                 255

Lys Val Gly Asp Lys Lys Val Ala His Thr Leu Val Leu Arg Lys Asp
            260                 265                 270

Gly Val Lys Lys Asn Ile Glu Leu Thr Glu Asn Glu Leu Val Phe Val
        275                 280                 285

Thr Asn Gly Ser Ile Thr Glu Ser Thr Thr Tyr Gly Asp Asn Asn Thr
    290                 295                 300

Pro Ala Pro Ile Asn Lys Asp Leu Gly Gly Ser Trp Ser Leu Trp Lys
305                 310                 315                 320

Asn Ile Ala Ala Gln Gly Glu Glu Phe Gly Arg Pro Glu Lys Phe Cys
                325                 330                 335

Asp Asn Leu Pro Glu Glu Ser Trp Phe Val Ser Ala Thr Leu Thr Thr
            340                 345                 350

Leu Asp Asp Arg Val Ala Pro Tyr Ile Glu Lys Ile Ser Lys Arg Asp
        355                 360                 365

Pro Tyr Ala Gly Lys Val Val Thr Gly Gly Ile Val Thr Ala Thr Asp
    370                 375                 380

Ser Asn Trp Met Leu Ser Tyr Thr Leu Asn Arg Gln Pro His Phe Arg
385                 390                 395                 400

Asn Gln Pro Lys Asp Gln Leu Val Val Trp Ile Tyr Gly Leu Leu Ser
                405                 410                 415

Asn Lys Pro Gly Asp Phe Ile Lys Lys Ser Ile Thr Glu Cys Thr Gly
            420                 425                 430

Ile Glu Ile Ala Gln Glu Trp Leu Tyr His Met Gly Val Pro Val Asp
        435                 440                 445

Glu Ile Pro Asp Ile Ala Gln Asn Ser Cys Asn Thr Ile Pro Cys Tyr
    450                 455                 460

Met Pro Tyr Ile Thr Ser Tyr Phe Met Pro Arg Ala Met Gly Asp Arg
465                 470                 475                 480

Pro Leu Val Val Pro Glu Gly Ser Ala Asn Leu Ala Phe Ile Gly Asn
                485                 490                 495

Phe Ser Glu Thr Ala Arg Asp Thr Val Phe Thr Thr Glu Tyr Ser Val
            500                 505                 510
```

```
Arg Thr Ala Met Glu Ala Val Tyr Gln Leu Leu Arg Ile Asp Arg Gly
            515                 520                 525

Val Pro Glu Val Phe Ala Ser Ala Phe Asp Val Arg Thr Leu Leu Ala
        530                 535                 540

Ser Thr Ala Arg Leu Leu Asp Gly Lys Lys Leu Thr Asp Ile Glu Ala
545                 550                 555                 560

Pro Phe Ile Leu Lys Gln Ile Gly Lys Leu Gly Ile His Lys Thr Lys
                565                 570                 575

Asp Thr Ile Ile Tyr Asp Leu Leu Lys Glu Ser Lys Leu Ile
            580                 585                 590

<210> SEQ ID NO 3
<211> LENGTH: 589
<212> TYPE: PRT
<213> ORGANISM: Macrococcus caseolyticus

<400> SEQUENCE: 3

Met Tyr Tyr Ser Asn Gly Asn Tyr Glu Ala Phe Ala Arg Pro Lys Lys
1               5                   10                  15

Pro Glu Gly Val Asp Asn Lys Ser Ala Tyr Leu Val Gly Ser Gly Leu
            20                  25                  30

Ala Ser Leu Ala Ala Ala Ser Phe Leu Ile Arg Asp Gly Gln Met Lys
        35                  40                  45

Gly Glu Asn Ile His Ile Leu Glu Glu Leu Asp Leu Pro Gly Gly Ser
    50                  55                  60

Leu Asp Gly Ile Leu Asn Pro Glu Arg Gly Tyr Ile Met Arg Gly Gly
65                  70                  75                  80

Arg Glu Met Glu Asn His Phe Glu Cys Leu Trp Asp Leu Phe Arg Ser
                85                  90                  95

Val Pro Ser Leu Glu Val Glu Asp Ala Ser Val Leu Asp Glu Phe Tyr
            100                 105                 110

Trp Leu Asn Lys Glu Asp Pro Asn Tyr Ser Lys Cys Arg Val Ile Glu
        115                 120                 125

Asn Arg Gly Gln Arg Leu Glu Ser Asp Gly Lys Met Thr Leu Thr Lys
    130                 135                 140

Lys Ala Asn Lys Glu Ile Ile Gln Leu Cys Leu Met Lys Glu Glu Gln
145                 150                 155                 160

Leu Asn Asp Val Lys Ile Ser Asp Val Phe Ser Lys Asp Phe Leu Asp
                165                 170                 175

Ser Asn Phe Trp Ile Tyr Trp Lys Thr Met Phe Ala Phe Glu Pro Trp
            180                 185                 190

His Ser Ala Met Glu Met Arg Arg Tyr Leu Met Arg Phe Ile His His
        195                 200                 205

Ile Gly Gly Leu Ala Asp Phe Ser Ala Leu Lys Phe Thr Lys Phe Asn
    210                 215                 220

Gln Phe Glu Ser Leu Val Met Pro Leu Ile Glu His Leu Lys Ala Lys
225                 230                 235                 240

Asn Val Thr Phe Glu Tyr Gly Val Thr Val Lys Asn Ile Gln Val Glu
                245                 250                 255

Cys Ser Lys Glu Ser Lys Val Ala Lys Ala Ile Asp Ile Val Arg Arg
            260                 265                 270

Gly Asn Glu Glu Ser Ile Pro Leu Thr Glu Asn Asp Leu Val Phe Val
        275                 280                 285

Thr Asn Gly Ser Ile Thr Glu Ser Thr Thr Tyr Gly Asp Asn Asp Thr
    290                 295                 300
```

```
Pro Ala Pro Pro Thr Ser Lys Pro Gly Gly Ala Trp Gln Leu Trp Glu
305                 310                 315                 320

Asn Leu Ser Thr Gln Cys Glu Glu Phe Gly Asn Pro Ala Lys Phe Tyr
                325                 330                 335

Lys Asp Leu Pro Glu Lys Ser Trp Phe Val Ser Ala Thr Ala Thr Thr
            340                 345                 350

Asn Asn Lys Glu Val Ile Asp Tyr Ile Gln Lys Ile Cys Lys Arg Asp
        355                 360                 365

Pro Leu Ser Gly Arg Thr Val Thr Gly Gly Ile Val Thr Val Asp Asp
370                 375                 380

Ser Asn Trp Gln Leu Ser Phe Thr Leu Asn Arg Gln Gln Phe Lys
385                 390                 395                 400

Asn Gln Pro Asp Asp Gln Val Ser Val Trp Ile Tyr Ala Leu Tyr Ser
                405                 410                 415

Asp Glu Arg Gly Glu Arg Thr Asn Lys Thr Ile Val Glu Cys Ser Gly
            420                 425                 430

Lys Glu Ile Cys Glu Glu Trp Leu Tyr His Met Gly Val Pro Glu Glu
        435                 440                 445

Lys Ile Ser Ala Leu Ala Ala Glu Cys Asn Thr Ile Pro Ser Tyr Met
450                 455                 460

Pro Tyr Ile Thr Ala Tyr Phe Met Pro Arg Lys Glu Gly Asp Arg Pro
465                 470                 475                 480

Leu Val Val Pro His Gly Ser Lys Asn Ile Ala Phe Ile Gly Asn Phe
                485                 490                 495

Ala Glu Thr Glu Arg Asp Thr Val Phe Thr Thr Glu Tyr Ser Val Arg
            500                 505                 510

Thr Ala Met Glu Ala Val Tyr Lys Leu Leu Glu Val Asp Arg Gly Val
        515                 520                 525

Pro Glu Val Phe Ala Ser Val Tyr Asp Val Arg Ile Leu Leu His Ala
530                 535                 540

Leu Ser Val Leu Asn Asp Gly Lys Lys Leu Asp Glu Ile Asp Met Pro
545                 550                 555                 560

Phe Tyr Glu Arg Leu Val Glu Lys Arg Leu Leu Lys Lys Ala Ser Gly
                565                 570                 575

Thr Phe Ile Glu Glu Leu Leu Glu Glu Ala Asn Leu Ile
            580                 585

<210> SEQ ID NO 4
<211> LENGTH: 591
<212> TYPE: PRT
<213> ORGANISM: Lactobacillus acidophilus

<400> SEQUENCE: 4

Met Tyr Tyr Ser Asn Gly Asn Tyr Glu Ala Phe Ala Asp Pro Lys Lys
1               5                   10                  15

Pro Ala Gly Val Asp Lys Lys Ser Ala Tyr Ile Ile Gly Ser Gly Leu
            20                  25                  30

Ala Gly Leu Ser Thr Ala Val Phe Leu Val Arg Asp Ala Gln Met Lys
        35                  40                  45

Gly Glu Asn Ile His Ile Leu Glu Glu Leu Pro Val Ala Gly Gly Ser
    50                  55                  60

Leu Asp Gly Ala Asp Arg Pro Asn Ala Gly Phe Val Val Arg Gly Gly
65                  70                  75                  80

Arg Glu Met Glu Asn His Phe Glu Cys Leu Trp Asp Met Tyr Arg Ser
```

```
                        85                  90                  95
Ile Pro Ser Leu Glu Val Pro Gly Ala Ser Tyr Leu Asp Glu Tyr Tyr
            100                 105                 110

Trp Leu Asp Lys Glu Asp Pro Asn Ser Ser Asn Cys Arg Leu Ile Tyr
            115                 120                 125

Asn Arg Gly Asp Arg Leu Pro Ser Asp Gly Gln Tyr Gly Leu Gly Lys
            130                 135                 140

Cys Ala Asn Glu Ile Val Lys Leu Ile Met Thr Pro Glu Lys Glu Ile
145                 150                 155                 160

Glu Gly Gln Thr Ile Glu Glu Phe Phe Ser Asp Glu Phe Phe Lys Thr
                165                 170                 175

Asn Phe Trp Thr Tyr Trp Ser Thr Met Phe Ala Phe Glu Lys Trp His
            180                 185                 190

Ser Leu Ala Glu Met Arg Arg Tyr Ala Met Arg Phe Ile His His Ile
                195                 200                 205

Asp Gly Leu Pro Asp Phe Thr Ala Leu Lys Phe Asn Lys Tyr Asn Gln
            210                 215                 220

Tyr Glu Ser Met Val Lys Pro Leu Leu Ala Tyr Leu Lys Asp His Gly
225                 230                 235                 240

Val Gln Phe Glu Tyr Asp Cys His Val Lys Asn Val Glu Val Asp His
                245                 250                 255

Glu Gly Asp Ser Lys Ile Ala Lys Lys Ile Val Met Thr Gln Asn Gly
            260                 265                 270

Lys Asp Lys Glu Ile Asp Leu Thr His Asn Asp Ile Val Phe Val Thr
            275                 280                 285

Asn Gly Ser Ile Thr Glu Ser Ser Thr Tyr Gly Asp Gln Asn Thr Pro
            290                 295                 300

Ala Pro Ile Thr Asn Ala Lys Gly Asp Ser Trp Lys Leu Trp Glu Asn
305                 310                 315                 320

Leu Ala Lys Gln Asp Pro Ala Phe Gly His Pro Asp Val Phe Cys Glu
                325                 330                 335

Asn Leu Pro Glu Arg Ser Trp Phe Val Ser Ala Thr Ala Thr Leu Glu
            340                 345                 350

Asn Lys Lys Leu Ala Pro Tyr Phe Glu Arg Leu Thr Lys Arg Ser Leu
            355                 360                 365

Tyr Asp Gly Lys Val Asn Thr Gly Gly Ile Ile Thr Ile Val Asp Ser
            370                 375                 380

Asn Trp Glu Leu Ser Phe Thr Ile His Arg Gln Pro His Phe Lys Ser
385                 390                 395                 400

Gln Asn Pro Asp Gln Ile Val Val Trp Ile Tyr Ala Leu Tyr Ser Asp
                405                 410                 415

Thr Glu Gly Asn Tyr Ile Lys Lys Arg Ile Val Asp Cys Thr Gly Lys
            420                 425                 430

Glu Ile Ala Glu Glu Leu Leu Tyr His Leu Gly Val Pro Glu Ser Gln
            435                 440                 445

Ile Ser Glu Leu Ala Ser Glu Glu Asn Met Asn Thr Val Pro Val Tyr
            450                 455                 460

Met Pro Tyr Ile Thr Ser Tyr Phe Met Pro Arg Arg Asp Gly Asp Arg
465                 470                 475                 480

Pro Asp Val Val Pro Glu Gly Ser Ile Asn Leu Ala Phe Ile Gly Asn
                485                 490                 495

Phe Ala Glu Ser Pro Thr Arg Asp Thr Val Phe Thr Thr Glu Tyr Ser
            500                 505                 510
```

```
Val Arg Thr Ala Met Glu Ala Val Tyr Thr Leu Leu Asn Val Asp Arg
    515                 520                 525

Gly Val Pro Glu Val Phe Asp Ser Ile Tyr Asp Ile Arg Gln Leu Leu
            530                 535                 540

Arg Ala Met Tyr Tyr Met Ser Asp Lys Lys Leu Ala Asp Gln Asp
545                 550                 555                 560

Met Pro Leu Pro Glu Lys Leu Ala Val Lys Thr Gly Met Arg Lys Ile
                565                 570                 575

Lys Lys Thr Trp Val Glu Glu Leu Leu Lys Glu Ala Asn Leu Val
                580                 585                 590

<210> SEQ ID NO 5
<211> LENGTH: 589
<212> TYPE: PRT
<213> ORGANISM: Stenotrophomonas maltophilia

<400> SEQUENCE: 5

Met Tyr Tyr Ser Ser Gly Asn Tyr Glu Ala Phe Ala Arg Pro Arg Lys
1               5                   10                  15

Pro Ala Gly Val Asp Gly Lys Arg Ala Trp Phe Val Gly Ser Gly Leu
            20                  25                  30

Ala Ser Leu Ala Gly Ala Ala Phe Leu Val Arg Asp Gly Arg Met Ala
        35                  40                  45

Gly Glu His Ile Thr Val Leu Glu Gln Gln Gln Ile Ala Gly Gly Ala
    50                  55                  60

Leu Asp Gly Leu Lys Val Pro Glu Lys Gly Phe Val Ile Arg Gly Gly
65                  70                  75                  80

Arg Glu Met Glu Asp His Phe Glu Cys Leu Trp Asp Leu Phe Arg Ser
                85                  90                  95

Ile Pro Ser Leu Glu Ile Glu Asp Ala Ser Val Leu Asp Glu Phe Tyr
            100                 105                 110

Trp Leu Asn Lys Asp Asp Pro Asn Tyr Ser Leu Gln Arg Ala Thr Ile
        115                 120                 125

Asn Arg Gly Glu Asp Ala His Thr Asp Gly Leu Phe Thr Leu Thr Glu
    130                 135                 140

Gln Ala Gln Lys Asp Ile Ile Ala Leu Phe Leu Ala Thr Arg Gln Glu
145                 150                 155                 160

Met Glu Asn Lys Arg Ile Asp Glu Val Leu Gly Arg Asp Phe Leu Asp
                165                 170                 175

Ser Asn Phe Trp Leu Tyr Trp Arg Thr Met Phe Ala Phe Glu Glu Trp
            180                 185                 190

His Ser Ala Leu Glu Met Lys Leu Tyr Leu His Arg Phe Ile His His
        195                 200                 205

Ile Gly Gly Leu Pro Asp Phe Ser Ala Leu Lys Phe Thr Lys Tyr Asn
    210                 215                 220

Gln Tyr Glu Ser Leu Val Leu Pro Leu Val Arg Trp Leu Gln Asp Gln
225                 230                 235                 240

Gly Val Val Phe Gln Tyr Gly Thr Glu Val Thr Asp Val Asp Phe Asp
                245                 250                 255

Leu Ala Ala Gly Arg Lys Gln Ala Thr Arg Ile His Trp Thr Arg Asp
            260                 265                 270

Gly Val Ala Gly Val Asp Leu Ser Ala Asp Asp Leu Val Phe Met
        275                 280                 285

Thr Ile Gly Ser Leu Thr Glu Asn Ser Asp Asn Gly Asp His His Thr
```

```
                290                 295                 300
Ala Ala Arg Leu Asn Glu Gly Pro Ala Pro Ala Trp Asp Leu Trp Arg
305                 310                 315                 320

Arg Ile Ala Ala Arg Asp Pro Ala Phe Gly Arg Pro Asp Val Phe Gly
                325                 330                 335

Ala His Ile Pro Gln Thr Lys Trp Glu Ser Ala Thr Val Thr Thr Leu
                340                 345                 350

Asp Ala Arg Ile Pro Ala Tyr Ile Gln Thr Ile Ala Lys Arg Asp Pro
                355                 360                 365

Phe Ser Gly Lys Val Val Thr Gly Gly Ile Val Ser Val Arg Asp Ser
370                 375                 380

Arg Trp Leu Met Ser Trp Thr Val Asn Arg Gln Pro His Phe Lys Asn
385                 390                 395                 400

Gln Pro Lys Asp Gln Ile Val Val Trp Val Tyr Ser Leu Phe Val Asp
                405                 410                 415

Thr Pro Gly Asp Tyr Val Lys Lys Pro Met Lys Glu Cys Thr Gly Glu
                420                 425                 430

Glu Ile Thr Arg Glu Trp Leu Tyr His Leu Gly Val Pro Val Glu Glu
                435                 440                 445

Ile Asp Glu Leu Ala Ala Thr Gly Ala Lys Thr Val Pro Val Met Met
450                 455                 460

Pro Tyr Ile Thr Ala Phe Phe Met Pro Arg Gln Ala Gly Asp Arg Pro
465                 470                 475                 480

Asp Val Val Pro Asp Gly Ala Val Asn Phe Ala Phe Ile Gly Gln Phe
                485                 490                 495

Ala Glu Ser Lys Gln Arg Asp Cys Ile Phe Thr Thr Glu Tyr Ser Val
                500                 505                 510

Arg Thr Pro Met Glu Ala Val Tyr Thr Leu Leu Gly Ile Glu Arg Gly
                515                 520                 525

Val Pro Glu Val Phe Asn Ser Thr Tyr Asp Val Arg Ser Leu Leu Ala
530                 535                 540

Ala Thr Gly Arg Leu Arg Asp Gly Lys Glu Leu Asp Ile Pro Gly Pro
545                 550                 555                 560

Ala Phe Leu Arg Asn Leu Leu Met Asn Lys Leu Asp Lys Thr Gln Ile
                565                 570                 575

Gly Gly Leu Leu Arg Glu Phe Lys Leu Val Gln Glu Asp
                580                 585

<210> SEQ ID NO 6
<211> LENGTH: 590
<212> TYPE: PRT
<213> ORGANISM: Streptococcus pyogenes

<400> SEQUENCE: 6

Met Tyr Tyr Thr Ser Gly Asn Tyr Glu Ala Phe Ala Thr Pro Arg Lys
1               5                   10                  15

Pro Glu Gly Val Asp Gln Lys Ser Ala Tyr Ile Val Gly Thr Gly Leu
                20                  25                  30

Ala Gly Leu Ala Ala Ala Val Phe Leu Ile Arg Asp Gly His Met Ala
                35                  40                  45

Gly Glu Arg Ile His Leu Phe Glu Glu Leu Pro Leu Ala Gly Gly Ser
                50                  55                  60

Leu Asp Gly Ile Glu Lys Pro His Leu Gly Phe Val Thr Arg Gly Gly
65                  70                  75                  80
```

```
Arg Glu Met Glu Asn His Phe Glu Cys Met Trp Asp Met Tyr Arg Ser
                 85                  90                  95

Ile Pro Ser Leu Glu Ile Pro Gly Ala Ser Tyr Leu Asp Glu Phe Tyr
            100                 105                 110

Trp Leu Asp Lys Asp Asp Pro Asn Ser Ser Asn Cys Arg Leu Ile His
            115                 120                 125

Lys Arg Gly Asn Arg Val Asp Asp Gly Gln Tyr Thr Leu Gly Lys
130             135                 140

Gln Ser Lys Glu Leu Ile His Leu Ile Met Thr Glu Glu Ser Leu
145                 150                 155                 160

Gly Asp Gln Thr Ile Glu Glu Phe Phe Ser Glu Asp Phe Phe Lys Ser
                165                 170                 175

Asn Phe Trp Val Tyr Trp Ala Thr Met Phe Ala Phe Glu Lys Trp His
            180                 185                 190

Ser Ala Val Glu Met Arg Arg Tyr Ala Met Arg Phe Ile His His Ile
            195                 200                 205

Asp Gly Leu Pro Asp Phe Thr Ser Leu Lys Phe Asn Lys Tyr Asn Gln
210                 215                 220

Tyr Asp Ser Met Val Lys Pro Ile Ile Ala Tyr Leu Glu Ser His Asp
225                 230                 235                 240

Val Asp Ile Gln Phe Asp Thr Lys Val Thr Asp Ile Gln Val Glu Gln
                245                 250                 255

Thr Ala Gly Lys Lys Val Ala Lys Thr Ile His Met Thr Val Ser Gly
                260                 265                 270

Glu Ala Lys Ala Ile Glu Leu Thr Pro Asp Asp Leu Val Phe Val Thr
            275                 280                 285

Asn Gly Ser Ile Thr Glu Ser Ser Thr Tyr Gly Ser His His Glu Val
290                 295                 300

Ala Lys Pro Thr Lys Ala Leu Gly Gly Ser Trp Asn Leu Trp Glu Asn
305                 310                 315                 320

Leu Ala Ala Gln Ser Asp Asp Phe Gly His Pro Lys Val Phe Tyr Gln
                325                 330                 335

Asp Leu Pro Ala Glu Ser Trp Phe Val Ser Ala Thr Ala Thr Ile Lys
            340                 345                 350

His Pro Ala Ile Glu Pro Tyr Ile Glu Arg Leu Thr His Arg Asp Leu
            355                 360                 365

His Asp Gly Lys Val Asn Thr Gly Gly Ile Ile Thr Ile Thr Asp Ser
370                 375                 380

Asn Trp Met Met Ser Phe Ala Ile His Arg Gln Pro His Phe Lys Glu
385                 390                 395                 400

Gln Lys Glu Asn Glu Thr Thr Val Trp Ile Tyr Gly Leu Tyr Ser Asn
                405                 410                 415

Ser Glu Gly Asn Tyr Val His Lys Lys Ile Glu Glu Cys Thr Gly Gln
            420                 425                 430

Glu Ile Thr Glu Glu Trp Leu Tyr His Leu Gly Val Pro Val Asp Lys
            435                 440                 445

Ile Lys Asp Leu Ala Ser Gln Glu Tyr Ile Asn Thr Val Pro Val Tyr
450                 455                 460

Met Pro Tyr Ile Thr Ser Tyr Phe Met Pro Arg Val Lys Gly Asp Arg
465                 470                 475                 480

Pro Lys Val Ile Pro Asp Gly Ser Val Asn Leu Ala Phe Ile Gly Asn
                485                 490                 495

Phe Ala Glu Ser Pro Ser Arg Asp Thr Val Phe Thr Thr Glu Tyr Ser
```

```
                    500                 505                 510
Ile Arg Thr Ala Met Glu Ala Val Tyr Ser Phe Leu Asn Gly Glu Arg
            515                 520                 525

Gly Ile Pro Gln Gly Phe Asn Ser Ala Tyr Asp Ile Arg Glu Leu Leu
        530                 535                 540

Lys Ala Phe Tyr Tyr Leu Asn Asp Lys Lys Ala Ile Lys Asp Met Asp
545                 550                 555                 560

Leu Pro Ile Pro Ala Leu Ile Glu Lys Ile Gly His Lys Lys Ile Lys
                    565                 570                 575

Asp Thr Phe Ile Glu Glu Leu Leu Lys Asp Ala Asn Leu Met
                580                 585                 590

<210> SEQ ID NO 7
<211> LENGTH: 625
<212> TYPE: PRT
<213> ORGANISM: Bifidobacterium breve

<400> SEQUENCE: 7

Met Tyr Tyr Ser Ser Gly Asn Tyr Glu Ala Phe Ala Arg Pro Lys Lys
1               5                   10                  15

Pro Ala Gly Val Asp Ser Lys His Ala Tyr Ile Ile Gly Thr Gly Leu
            20                  25                  30

Ala Ala Leu Ser Ser Ala Cys Tyr Leu Val Arg Asp Gly Gln Met Pro
        35                  40                  45

Gly Asp His Ile His Ile Leu Glu Lys Asp Pro Val Pro Gly Gly Ala
    50                  55                  60

Cys Asp Gly Leu Asp Ile Pro Gly Leu Gly Tyr Val Met Arg Gly Gly
65                  70                  75                  80

Arg Glu Met Asp Asn His Phe Glu Val Met Trp Asp Leu Phe Arg Ser
                85                  90                  95

Ile Pro Ser Ile Glu Thr Glu Gly Val Ser Val Leu Asp Glu Tyr Tyr
            100                 105                 110

Trp Leu Asn Lys Glu Asp Pro Asn Tyr Ser Leu Cys Arg Ala Thr Lys
        115                 120                 125

Asp Leu Gly Lys Asp Ala Gly Leu Lys Gly Lys Phe Gly Leu Ser Asp
    130                 135                 140

Lys Ala Ser Met Glu Ile Met Lys Leu Phe Phe Thr Pro Asp Glu Asp
145                 150                 155                 160

Leu Tyr Asp Lys Pro Ile Thr Asp Phe Phe Asp Glu Val Leu Asn
                165                 170                 175

Ser Asn Phe Trp Leu Tyr Trp Arg Thr Met Phe Ala Phe Glu Asn Trp
            180                 185                 190

His Ser Ala Leu Glu Met Lys Leu Tyr Ile Lys Arg Tyr Ile His His
        195                 200                 205

Ile Gly Gly Leu Pro Asp Phe Ser Ala Leu Arg Phe Thr Arg Tyr Asn
    210                 215                 220

Gln Tyr Glu Ser Met Ile Leu Pro Met Val Lys Tyr Leu Glu Ser His
225                 230                 235                 240

Gly Val Glu Phe Arg Tyr Asn Thr Lys Val Glu Asn Val Glu Phe Ala
                245                 250                 255

Ile Gly Gly Gly Asp Gly Pro Lys Arg Glu His Thr Gly Ile Gly Gln
            260                 265                 270

Asp Thr Ile Gln Lys Ile Gln Ala Thr Ser Gly Phe Phe Lys Arg Asn
        275                 280                 285
```

```
Pro Ala Ser Thr Pro Thr Lys Lys Leu Ala Val Arg Ile Asp Val Ser
    290                 295                 300
Gln Glu Gly Glu Lys Ser Ser Ile Asp Leu Thr Glu Asn Asp Leu Val
305                 310                 315                 320
Phe Ile Thr Asn Gly Gly Cys Val Glu Asn Ser Thr Met Gly Ser Gln
                325                 330                 335
Asn Ser Pro Ala Ala Trp Asn Pro Asp Leu Lys Pro Gly Gly Gly Trp
            340                 345                 350
Asp Met Trp Arg Arg Ile Ala Glu Gln Asp Pro Ser Phe Gly His Pro
        355                 360                 365
Glu Lys Phe Cys Ser Asp Pro Asn Ala Thr Lys Trp Met Ser Ala Thr
370                 375                 380
Val Thr Thr Leu Asp Asp Glu Ile Pro Pro Tyr Ile Gln Lys Ile Cys
385                 390                 395                 400
Lys Arg Asp Pro Phe Ser Gly Lys Val Val Thr Gly Ile Val Thr
                405                 410                 415
Val Gln Asp Ser Asn Trp Leu Met Ser Trp Thr Leu Asn Arg Gln Gln
            420                 425                 430
Gln Phe Arg Asp Gln Pro Lys Asp Gln Leu Cys Val Trp Val Tyr Gly
        435                 440                 445
Leu Phe Pro Asp Lys Pro Gly Asn Tyr Val Lys Pro Met Thr Glu
450                 455                 460
Cys Thr Gly Glu Glu Ile Cys Glu Glu Trp Leu Tyr His Met Gly Val
465                 470                 475                 480
Pro Thr Asp Lys Ile Glu Pro Leu Ala Lys His His Ala Asn Thr Val
                485                 490                 495
Pro Val Met Met Pro Tyr Ile Thr Ala Phe Phe Met Pro Arg Ala Ala
            500                 505                 510
Gly Asp Arg Pro Asp Val Val Pro Asp Gly Ala Val Asn Phe Ala Phe
        515                 520                 525
Leu Gly Gln Phe Ala Glu Thr Pro Arg Asp Thr Ile Phe Thr Thr Glu
530                 535                 540
Tyr Ser Met Arg Thr Gly Met Glu Ala Val Tyr Thr Leu Leu Gly Val
545                 550                 555                 560
Asp Arg Gly Val Pro Glu Val Trp Gly Ser Val Tyr Asp Val Arg Asn
                565                 570                 575
Leu Leu Asn Ala Thr Val Lys Leu Arg Asp Gly Ala Pro Val Thr Asp
            580                 585                 590
Met Lys Leu Asn Phe Ile Glu Lys Ala Val Lys Lys Val Leu Lys
        595                 600                 605
Lys Leu Asp Gly Thr Asp Ile Ala Thr Leu Leu Arg Glu Tyr His Val
610                 615                 620
Ile
625

<210> SEQ ID NO 8
<211> LENGTH: 732
<212> TYPE: PRT
<213> ORGANISM: Bifidobacterium animalis subsp. lactis (strain BB-12)

<400> SEQUENCE: 8

Met Asp Thr Arg Ala Pro Lys Val Gly Ala Gly Lys Ser Ser Arg Glu
1               5                   10                  15
Arg Ala Arg Ala Arg Gly Gly Ala Met Tyr Tyr Ser Ala Gly Asn Phe
            20                  25                  30
```

```
Glu Ala Phe Ala His Pro Lys Lys Pro Glu Gly Leu Glu Asn Lys Ser
         35                  40                  45

Ala Tyr Ile Ile Gly Thr Gly Leu Ala Ala Leu Thr Ala Ala Phe Tyr
 50                  55                  60

Leu Val Arg Asp Ala Gln Met Pro Gly Lys Asn Ile His Val Phe Asp
 65                  70                  75                  80

Lys Asp Val Val Pro Gly Gly Ala Leu Asp Gly Ala Phe Ile Lys Gly
                     85                  90                  95

Glu Gly Tyr Val Met Arg Gly Gly Arg Glu Met Asp Asn His Phe Glu
                 100                 105                 110

Val Met Trp Asp Val Tyr Arg Asp Val Pro Ser Ile Glu Asp Pro Asn
                 115                 120                 125

Val Ser Met Leu Asp His Tyr Tyr Trp Leu Asn Lys Glu Asp Pro Asn
             130                 135                 140

Tyr Ser Lys Cys Arg Ala Thr Lys Ala Arg Gly His Asn Ala His Thr
 145                 150                 155                 160

Asp Asn Lys Phe Asn Leu Ser Asp Lys Gly Cys Met Glu Ile Leu Lys
                 165                 170                 175

Leu Tyr Leu Ala Ser Glu Asp Glu Leu Ala Asn Lys Lys Ile Thr Asp
             180                 185                 190

Tyr Phe Asp Asp Glu Val Leu Asn Ser Asn Phe Trp Leu Tyr Trp Arg
                 195                 200                 205

Thr Met Phe Ala Phe Glu Asn Trp Asp Ser Ala Leu Glu Met His Arg
 210                 215                 220

Tyr Ile His Arg Phe Ile His Ile Gly Gly Leu Pro Asp Phe Ser
225                 230                 235                 240

Ala Leu Arg Phe Thr Arg Tyr Asn Gln Tyr Glu Ser Met Ile Leu Pro
                 245                 250                 255

Leu Met Asn Tyr Leu Lys Ala His Asp Val Gln Phe His Met Gly Thr
             260                 265                 270

Ala Val Asp Asp Val Thr Phe Ala Ile Ser Asp His Glu Asn Gly Pro
             275                 280                 285

Val Arg Asn Val Phe Thr Asn Val Ser Met Asp Glu Ala Gln Arg Ala
         290                 295                 300

Gln Ala Glu Asn Gly Ala Phe Pro Arg Asn Pro Tyr Ser Thr Pro Asn
305                 310                 315                 320

Lys Lys Val Ala Lys Thr Leu Val Ile Thr Asp Leu Val Lys Asn Glu
                 325                 330                 335

Arg Lys Thr Ile Glu Leu Thr Glu Asp Phe Val Phe Ile Thr Asn
                 340                 345                 350

Gly Gly Leu Val Glu Ser Thr Thr Glu Gly Asp Gln Asn Thr Pro Ala
             355                 360                 365

Gly Phe Asp Pro Thr Leu Lys Pro Gly Asn Gly Trp Asp Met Trp Asn
 370                 375                 380

Arg Ile Ala Ala Val Asp Pro Ser Phe Gly His Pro Glu Lys Phe Ile
385                 390                 395                 400

Tyr Asp Pro Asn Leu Thr Lys Trp Met Ser Ala Thr Ala Thr Leu
                 405                 410                 415

Asp Asp Thr Ile Pro Ala Tyr Ile Glu Lys Ile Thr Gly Arg Ser Pro
             420                 425                 430

Phe Gly Gly His Thr Val Thr Gly Gly Ile Val Thr Val Glu Asp Ser
             435                 440                 445
```

```
Asn Trp Leu Met Ser Trp Thr Val Asn Arg Gln Gln Gln Phe Arg Asn
            450                 455                 460

Gln Pro Lys Asp Met Ile Ser Ala Trp Ile Tyr Gly Leu Phe Pro Asp
465                 470                 475                 480

Lys Pro Gly Asn Tyr Ile Arg Lys Pro Met Gln Asp Cys Thr Gly Met
                485                 490                 495

Glu Ile Cys Glu Glu Trp Leu Tyr His Met Gly Val Pro Glu Glu Gln
            500                 505                 510

Ile Glu Glu Leu Ala Lys Asn His Cys Asn Thr Val Pro Val Met Met
            515                 520                 525

Pro Tyr Val Asp Ala Phe Phe Met Pro Arg Glu Leu Gly Asp Arg Pro
530                 535                 540

Asp Val Val Pro Asp Gly Ala Val Asn Phe Ala Phe Ile Gly Gln Phe
545                 550                 555                 560

Ala Glu Glu Pro Arg Asp Thr Ile Phe Thr Thr Glu Tyr Ser Met Arg
                565                 570                 575

Thr Gly Met Glu Ala Val Tyr Thr Leu Cys Asp Val Asp Arg Gly Val
            580                 585                 590

Pro Glu Val Trp Asn Ser Glu Tyr Asp Val Arg Asp Met Leu Asn Ala
            595                 600                 605

Ala Val Lys Leu Arg Asp Gly Gln Pro Leu Thr Thr Phe Gly Arg Asn
610                 615                 620

Asn Val Glu Arg Lys Ala Ile Ala Phe Ala Leu Gly Arg Thr Arg Gly
625                 630                 635                 640

Thr Tyr Ile Tyr Asp Met Leu Lys Val Tyr Gly Ala Ile Ala Asp Pro
                645                 650                 655

Lys His Pro Val Asp Met Lys Pro Gly Met Arg Phe Asp Glu Ser Phe
            660                 665                 670

Asn Glu Ala Asp Glu Gln Arg Leu Met Gln His Ala Lys Glu Ala Glu
            675                 680                 685

Ala Glu Ala Phe Ala Thr Pro Cys Ser Ala Asp Ala Pro Val Ala Ala
            690                 695                 700

Asp Thr Val Asp Thr Val Asp Thr Val Ala Pro Ala Ala Ala Pro Asp
705                 710                 715                 720

Gly Ala Leu Glu Pro Gly Glu Asn Asp Ser Ala Lys
                725                 730

<210> SEQ ID NO 9
<211> LENGTH: 569
<212> TYPE: PRT
<213> ORGANISM: Lactobacillus plantarum subsp. plantarum ST-III

<400> SEQUENCE: 9

Met Gly Ala Leu Phe Met Val Lys Ser Lys Ala Ile Met Ile Gly Ala
1               5                   10                  15

Gly Leu Ser Asn Met Ala Ala Val Tyr Leu Ile Gln Asp Gly His
                20                  25                  30

Trp Asp Gly Lys Asp Ile Thr Phe Tyr Gly Val Asp Met His Gly Ala
            35                  40                  45

Asn Asp Gly Gly Ala Thr Thr Asp Phe Thr Asn Glu Tyr Trp Asn Lys
50                  55                  60

Asn His Pro Met Ala Asn Thr Thr Gly Tyr Val Ala Arg Gly Arg
65                  70                  75                  80

Met Leu Asn Tyr Arg Thr Tyr Val Asp Leu Met Asp Leu Leu Asp Arg
                85                  90                  95
```

```
Ile Pro Ser Val Thr Glu Pro Gly Met Thr Ala Ala Glu Asp Thr Arg
                100                 105                 110

Asp Phe Asp Ala Lys His Arg Thr Tyr Asp Ile Ala Arg Leu Met Gln
            115                 120                 125

Gly Gly Lys Gly Ile Ile Asn Ala Gly Lys Leu Gly Phe Asn Asn Lys
        130                 135                 140

Asp Arg Thr Leu Leu Thr Lys Leu Ile Met Met Pro Asp Ser Glu Glu
145                 150                 155                 160

Thr Lys Leu Asp Asn Val Ser Ile Ala Glu Tyr Phe Lys Asp Asp Pro
                165                 170                 175

His Met Phe Gln Thr Asn Phe Trp Tyr Met Trp Glu Thr Thr Phe Ala
            180                 185                 190

Phe Arg Thr Gln Ser Ser Ala Gln Glu Leu Arg Arg Tyr Met His Gln
        195                 200                 205

Met Ile Tyr Glu Phe Thr Gln Ile Glu His Leu Val Gly Val Asn Arg
        210                 215                 220

Thr Arg Tyr Asn Gln Phe Glu Ser Met Ile Leu Pro Leu Ile Lys Tyr
225                 230                 235                 240

Leu Gln Gly Gln Gly Val Thr Phe Ile Asp Asn Lys Ile Val Lys Asp
                245                 250                 255

Trp Gln Phe Lys Asp Thr Pro Met Gln Asp Glu Ile Thr Val Thr Gly
            260                 265                 270

Leu Val Ile Glu Asp Ala Gln Thr Gly Glu Thr Glu Glu Val Glu Val
        275                 280                 285

Asp Glu Asp Thr Ala Val Ile Phe Thr Asn Gly Ser Ile Thr Asp Ser
        290                 295                 300

Ala Thr Met Gly Asp Tyr Asn Thr Pro Ala Pro Glu Asn Met Asp Tyr
305                 310                 315                 320

Gly Val Ser Ala Ser Leu Trp Lys Lys Ala Thr Glu Arg Phe Tyr Asn
                325                 330                 335

Leu Gly Thr Pro Asp Lys Phe Phe Asn Asp Arg Asn Ala Ser Glu Trp
            340                 345                 350

Val Ser Phe Thr Leu Thr Thr Lys Asn His Leu Phe Leu Asn Glu Ile
        355                 360                 365

Val Arg Ile Thr Thr Gln Glu Pro Gly Asn Ala Leu Asn Ser Phe Leu
        370                 375                 380

Ser Thr Thr Pro Ile Thr Pro Leu Asn Gln Lys Asp Val Asn Met Ser
385                 390                 395                 400

Ile Val Val His His Gln Pro His Phe Thr Thr Gln Pro Asn Glu
                405                 410                 415

Thr Val Leu Trp Gly Tyr Phe Leu Tyr Pro Arg Arg Gln Gly Glu Phe
            420                 425                 430

Val Asn Lys Pro Tyr Ile Lys Met Thr Gly Lys Glu Met Ala Gln Glu
        435                 440                 445

Leu Ile Gly Gln Leu Ser Lys Val Asp Pro Gly Pro Gly Asn Ile Lys
        450                 455                 460

Asp Lys Glu Lys Glu Ile Leu Asp Ser Ile Val Asn Asn Ile Pro Val
465                 470                 475                 480

Tyr Met Pro Tyr Ala Ser Ala Leu Phe Asn Asn Arg Ala Lys Ser Asp
                485                 490                 495

Arg Pro Glu Val Leu Pro Lys His Ser Thr Asn Leu Ala Phe Thr Gly
            500                 505                 510
```

```
Glu Phe Ala Glu Gln Pro Tyr Gln Met Ile Phe Thr Glu Gln Ser Ala
            515                 520                 525

Val Arg Ser Gly Glu Ile Ala Ala Tyr His Phe Ala Gly Val Pro Met
530                 535                 540

Asp Asn Leu Val Lys Thr Pro Arg Tyr Asp Lys Asp Pro Lys Thr Leu
545                 550                 555                 560

Leu Lys Ala Thr Lys Lys Met Phe Asp
                565

<210> SEQ ID NO 10
<211> LENGTH: 564
<212> TYPE: PRT
<213> ORGANISM: Lactobacillus rhamnosus LGG

<400> SEQUENCE: 10

Met Ile Lys His Lys Ala Ile Met Ile Gly Ala Gly Leu Ala Asn Met
1               5                   10                  15

Ala Ala Ala Val Tyr Leu Ile Gln Glu Gly His Trp Gln Gly Asp Gln
                20                  25                  30

Ile Thr Phe Tyr Ser Leu Asp Asp His Gly Ser Asn Asp Gly Ala Pro
            35                  40                  45

Ala Glu Glu Thr Ala Asp Glu Tyr Trp Asn Lys Tyr His Pro Met Glu
50                  55                  60

Asn Thr Lys Gly Tyr Val Ala Arg Gly Arg Met Leu Asn Tyr Arg
65                  70                  75                  80

Thr Tyr Val Asp Leu Met Asp Leu Leu Ser Arg Ile Pro Ser Ala Thr
                85                  90                  95

Glu Pro Gly Leu Thr Ala Glu Asp Thr Arg Gln Phe Asp Ala Gln
            100                 105                 110

His Arg Thr Phe Asp Lys Ala Arg Leu Met Glu Gly Gly Ile Gly Ile
        115                 120                 125

Ile Gln Ala Gly His Leu Gly Leu Asn Asn Lys Asp Arg Leu Leu Leu
130                 135                 140

Thr Lys Leu Ile Met Met Pro Asp Ser Glu Glu Lys Leu Asp Asn
145                 150                 155                 160

Val Ser Ile Ala Asp Tyr Phe Lys Asp Asp Pro His Met Phe Gln Thr
                165                 170                 175

Asn Phe Trp Tyr Met Trp Glu Thr Thr Phe Ala Phe Arg Val Glu Ser
            180                 185                 190

Ser Ala Gln Glu Leu Arg Arg Tyr Met His Met Met Ile Tyr Glu Phe
        195                 200                 205

Thr Gln Ile Glu His Leu Val Gly Val Asn Arg Thr Arg Tyr Asn Gln
210                 215                 220

Phe Glu Ser Ile Met Leu Pro Leu Ile Asn Tyr Leu Lys Asp Gln Gly
225                 230                 235                 240

Cys Arg Ile Ile Leu Asn Arg Arg Val Thr Ala Phe Glu Phe Lys Asp
                245                 250                 255

Thr Ala Met Thr Asp Glu Ile Thr Val Thr Gly Leu Lys Met Leu Asn
            260                 265                 270

Thr Glu Thr Asp Lys Pro Glu His Val Val Val Asp Asp Thr Ala
        275                 280                 285

Val Phe Phe Thr Asn Gly Ser Ile Thr Asp Ser Ala Thr Gln Gly Asp
290                 295                 300

Phe Asp His Pro Ala Val Glu Asn Met Asp Tyr Gly Ala Ala Ala Ser
305                 310                 315                 320
```

Leu Trp Lys Gln Ala Thr Asp His Phe Tyr Asn Leu Gly Asn Pro Asp
                325                 330                 335

Lys Phe Phe Ala Asp Arg Ala Ala Ser Glu Trp Val Ser Phe Thr Leu
            340                 345                 350

Thr Thr Lys Asp His Leu Leu Leu Asn Glu Ile Glu Arg Ile Thr Thr
        355                 360                 365

Gln Ile Pro Gly Asn Ala Leu Asn Ser Phe Leu Ser Thr Gln Pro Ile
    370                 375                 380

Thr Ala Leu Gly Gln Lys Asp Val Met Met Ser Ile Val Val His His
385                 390                 395                 400

Gln Pro His Phe Thr Thr Gln Lys Pro Asn Glu Thr Val Leu Trp Gly
                405                 410                 415

Tyr Phe Leu Tyr Pro Arg Arg Tyr Gly Glu Phe Val Asn Lys Pro Tyr
            420                 425                 430

Ile Lys Met Thr Gly Lys Glu Met Ala Leu Glu Leu Ile Gly Gln Leu
        435                 440                 445

Ala Lys Val Asp Pro Gly Pro Gly Asn Ile Arg Asp Arg Gln Asp Glu
    450                 455                 460

Ile Met Ala Ser Ile Ile Asn Asn Ile Pro Val Tyr Met Pro Tyr Ala
465                 470                 475                 480

Ser Ala Leu Phe Asn Asn Arg Ala Lys Val Asp Arg Pro Glu Val Ile
                485                 490                 495

Pro Ala His Ser Thr Asn Leu Ala Phe Thr Gly Glu Phe Ala Glu Gln
            500                 505                 510

Pro Phe Gln Met Val Phe Thr Glu Gln Ser Ala Val Arg Ser Gly Glu
        515                 520                 525

Ile Ala Ala Tyr His Phe Thr Gly Ile Pro Met Ser His Leu Val His
    530                 535                 540

Thr Pro Arg Tyr Asp Lys Asp Ile Lys Thr Leu Met Arg Ala Thr Lys
545                 550                 555                 560

Lys Met Phe Glu

<210> SEQ ID NO 11
<211> LENGTH: 564
<212> TYPE: PRT
<213> ORGANISM: Lactobacillus casei W56

<400> SEQUENCE: 11

Met Ile Lys His Lys Ala Ile Met Ile Gly Ala Gly Leu Ala Asn Met
1               5                   10                  15

Ala Ala Ala Val Tyr Leu Ile Gln Glu Ala His Trp Gln Gly Asp Gln
            20                  25                  30

Ile Thr Phe Tyr Ser Leu Asp Asp His Gly Ser Asn Asp Gly Ala Pro
        35                  40                  45

Thr Val Asp Thr Val Asp Glu Tyr Trp Asn Lys Asn His Pro Met Glu
    50                  55                  60

Asn Thr Lys Gly Tyr Val Ala Arg Gly Gly Arg Met Leu Asn Tyr Arg
65                  70                  75                  80

Thr Tyr Val Asp Leu Met Asp Leu Leu Ser Arg Ile Pro Ser Ala Thr
                85                  90                  95

Glu Pro Gly Leu Thr Ala Glu Glu Asp Thr Arg Gln Phe Asp Ala Gln
            100                 105                 110

His Arg Thr Phe Asp Lys Ala Arg Leu Met Glu Gly Gly Ile Gly Ile
        115                 120                 125

```
Ile Gln Ala Gly His Leu Gly Leu Asn Asn Thr Asp Arg Leu Leu Leu
        130                 135                 140

Thr Lys Leu Ile Met Met Pro Asp Ser Glu Glu Lys Leu Asp Asn
145                 150                 155                 160

Val Ser Ile Ala Asp Tyr Phe Lys Asp Pro His Met Phe Gln Thr
                165                 170                 175

Asn Phe Trp Tyr Met Trp Glu Thr Thr Phe Ala Phe Arg Thr Gln Ser
                180                 185                 190

Ser Ala Gln Glu Leu Arg Arg Tyr Met His Met Met Ile Tyr Glu Phe
        195                 200                 205

Thr Gln Ile Glu His Leu Val Gly Val Asn Arg Thr Arg Tyr Asn Gln
210                 215                 220

Phe Glu Ser Ile Met Leu Pro Leu Ile Asn Tyr Leu Lys Glu Gln Gly
225                 230                 235                 240

Cys Lys Ile Ile Leu Asn Arg Arg Val Thr Ala Phe Glu Phe Glu Asp
                245                 250                 255

Thr Ala Met Thr Asp Glu Ile Thr Val Thr Gly Leu Thr Ile Leu Asn
                260                 265                 270

Thr Glu Thr Asp Asp Glu Glu His Val Thr Val Asp Asp Thr Ala
        275                 280                 285

Val Phe Phe Thr Asn Gly Ser Ile Thr Asp Ser Ala Thr Gln Gly Asp
        290                 295                 300

Phe Asp His Ala Ala Val Glu Asn Met Asp Tyr Gly Ala Ala Ala Ser
305                 310                 315                 320

Leu Trp Lys Gln Ala Thr Glu His Phe Tyr Asn Leu Gly Asn Pro Asp
                325                 330                 335

Lys Phe Phe Ala Asp Arg Ser Ala Ser Glu Trp Val Ser Phe Thr Leu
                340                 345                 350

Thr Thr Lys Asp His Leu Leu Leu Asn Glu Ile Glu Arg Ile Thr Thr
                355                 360                 365

Gln Val Pro Gly Asn Ala Leu Asn Ser Phe Met Ser Thr Gln Pro Ile
        370                 375                 380

Thr Ala Leu Gly Gln Lys Asp Val Met Met Ser Ile Val Val His His
385                 390                 395                 400

Gln Pro His Phe Thr Thr Gln Lys Pro Asn Glu Thr Val Leu Trp Gly
                405                 410                 415

Tyr Phe Leu Tyr Pro Arg Arg Tyr Gly Glu Phe Val Asn Lys Pro Tyr
                420                 425                 430

Ile Glu Met Thr Gly Lys Glu Met Ala Leu Glu Leu Ile Gly Gln Leu
                435                 440                 445

Ala Lys Val Asp Pro Gly Pro Gly Asn Ile Arg Asp His Gln Asp Glu
        450                 455                 460

Ile Met Ala Ser Ile Ile Asn Asn Ile Pro Val Tyr Met Pro Tyr Ala
465                 470                 475                 480

Ser Ala Leu Phe Asn Asn Arg Ala Lys Val Asp Arg Pro Asp Val Ile
                485                 490                 495

Pro Ala His Ser Thr Asn Leu Ala Phe Thr Gly Glu Phe Ala Glu Gln
                500                 505                 510

Pro Phe Gln Met Val Phe Thr Glu Gln Ser Ala Val Arg Ser Gly Glu
        515                 520                 525

Ile Ala Ala Tyr His Phe Thr Gly Ile Pro Met Ser His Leu Val Lys
530                 535                 540
```

Thr Pro Arg Tyr Asp Lys Asp Ile Lys Thr Leu Met Arg Ala Thr Lys
545                 550                 555                 560

Lys Met Phe Glu

<210> SEQ ID NO 12
<211> LENGTH: 591
<212> TYPE: PRT
<213> ORGANISM: Lactobacillus delbrueckii subsp. bulgaricus

<400> SEQUENCE: 12

Met Tyr Tyr Ser Asn Gly Asn Tyr Glu Ala Phe Thr Asp Ala Arg Lys
1               5                   10                  15

Pro Lys Asp Ala Asp Lys Lys Ser Ala Tyr Val Ile Gly Gly Gly Leu
            20                  25                  30

Ala Gly Leu Ala Ala Cys Val Phe Met Ile Arg Asp Gly His Met Asp
        35                  40                  45

Gly Lys Lys Ile His Leu Leu Glu Glu Ala Leu Ala Gly Gly Ser
    50                  55                  60

Leu Asp Gly Thr Lys Arg Pro Glu Tyr Gly Tyr Ile Ile Arg Gly Gly
65                  70                  75                  80

Arg Glu Met Glu Asn His Phe Glu Cys Leu Trp Asp Met Tyr Arg Ser
                85                  90                  95

Ile Pro Ser Leu Glu Ile Pro Gly Ala Ser Tyr Leu Asp Glu Tyr Ala
            100                 105                 110

Trp Leu Asp Lys Asp Pro Asn Ser Ser Asn Cys Arg Leu Ile His
        115                 120                 125

His Arg Gly Asp Arg Val Pro Thr Asp Gly Gln Tyr Gly Leu Gly Lys
130                 135                 140

Cys Ala Gly Glu Ile Val Lys Leu Ile Met Thr Pro Glu Asp Lys Leu
145                 150                 155                 160

Glu Gly Ile Ser Ile Glu Asp Phe Phe Ser Asp Glu Phe Phe Glu Thr
                165                 170                 175

Asn Phe Trp Ala Tyr Trp Ala Thr Met Phe Ala Phe Glu Lys Trp His
            180                 185                 190

Ser Val Ile Glu Met Arg Arg Tyr Ala Met Arg Phe Ile His His Ile
        195                 200                 205

Asp Gly Leu Pro Asp Leu Ser Ala Leu Lys Phe Asn Lys Tyr Asn Gln
210                 215                 220

Tyr Glu Ser Met Thr Lys Pro Leu Leu Ala Tyr Leu Glu Ser His Asp
225                 230                 235                 240

Val Asp Ile Cys Tyr Asn Thr Gln Val Glu Asn Val Val Asp Thr
                245                 250                 255

Ser Asn Gly Glu Lys Val Ala Lys Lys Leu Ile Leu Thr Arg Asp Gly
            260                 265                 270

Glu His Gln Glu Ile Asp Leu Thr Pro Asp Asp Leu Val Tyr Val Thr
        275                 280                 285

Asn Gly Ser Ile Val Glu Ser Ser Thr Tyr Gly Thr His His Thr Pro
290                 295                 300

Ala Pro Ile Thr His Lys Leu Gly Gly Ser Trp His Leu Trp Gln Asn
305                 310                 315                 320

Leu Ala Glu Gln Asp Glu Ala Phe Gly His Pro Glu Val Phe Cys Glu
                325                 330                 335

Asn Ile Pro Glu Arg Ala Trp Phe Val Ser Ala Thr Met Thr Met Lys
            340                 345                 350

-continued

```
Asp Ala Thr Leu Glu Pro Tyr Phe Glu Arg Leu Thr Lys Arg Asp Ile
        355                 360                 365

His Gln His Arg Val Asn Thr Gly Gly Ile Ile Thr Val Thr Asp Ser
    370                 375                 380

Asn Trp Met Leu Ser Phe Thr Ile His Arg Gln Pro His Phe Lys Asp
385                 390                 395                 400

Gln Lys Glu Asn Glu Thr Val Val Trp Ile Tyr Ala Leu Tyr Ser Asp
                405                 410                 415

Thr Pro Gly Asn Tyr Ile Lys Lys Arg Val Val Asp Cys Thr Gly Glu
                420                 425                 430

Glu Ile Thr Glu Glu Leu Leu Tyr His Leu Gly Val Pro Asp Asp Leu
        435                 440                 445

Ile Lys Lys Tyr Ala Gly Asp Asp Tyr Val Asn Thr Val Pro Val Tyr
    450                 455                 460

Met Pro Tyr Ile Thr Ala Tyr Phe Gln Met Arg Lys Lys Gly Asp Arg
465                 470                 475                 480

Pro Ala Val Val Pro Ala Gly Ser Val Asn Leu Ala Phe Ile Gly Asn
                485                 490                 495

Phe Ala Glu Ser Pro Thr Arg Asp Thr Val Phe Thr Thr Glu Tyr Ser
                500                 505                 510

Val Arg Thr Ala Met Glu Ala Val Tyr Thr Leu Leu Asn Val Asp Arg
        515                 520                 525

Gly Val Pro Glu Val Phe Asp Ser Val Tyr Asp Ile Arg Glu Leu Leu
        530                 535                 540

Lys Ala Thr Tyr Tyr Leu Asn Asp Lys Lys Pro Ile Asp Gln Met Asp
545                 550                 555                 560

Leu Pro Leu Pro Lys Ile Val Val Lys Gly Ala Met Lys Lys Val Gln
                565                 570                 575

Gly Thr Trp Leu Glu Glu Leu Leu Lys Glu Ala Lys Leu Leu Glu
        580                 585                 590
```